(12) United States Patent
Hariri et al.

(10) Patent No.: US 11,953,441 B2
(45) Date of Patent: Apr. 9, 2024

(54) OPTICAL REAL-TIME BIOSENSOR

(71) Applicants: CZ Biohub SF LLC, San Francisco, CA (US); The Board of Trustees of the Leland Stanford Junior University, Stanford, CA (US)

(72) Inventors: Amani Hariri, Stanford, CA (US); Constantin Dory, Stanford, CA (US); Alyssa Cartwright, Stanford, CA (US); Jelena Vuckovic, Stanford, CA (US); Hyongsok Tom Soh, Stanford, CA (US)

(73) Assignees: CZ Biohub SF, LLC, San Francisco, CA (US); The Board of Trustees of the Leland Stanford Junior University, Stanford, CA (US)

( * ) Notice: Subject to any disclaimer, the term of this patent is extended or adjusted under 35 U.S.C. 154(b) by 345 days.

(21) Appl. No.: 17/286,912

(22) PCT Filed: Oct. 23, 2019

(86) PCT No.: PCT/US2019/057728
§ 371 (c)(1),
(2) Date: Apr. 20, 2021

(87) PCT Pub. No.: WO2020/086764
PCT Pub. Date: Apr. 30, 2020

(65) Prior Publication Data
US 2021/0372929 A1 Dec. 2, 2021

Related U.S. Application Data

(60) Provisional application No. 62/750,056, filed on Oct. 24, 2018.

(51) Int. Cl.
*G01N 21/64* (2006.01)
*A61B 5/00* (2006.01)
*A61B 5/1455* (2006.01)

(52) U.S. Cl.
CPC ....... *G01N 21/6486* (2013.01); *A61B 5/0059* (2013.01); *A61B 5/1455* (2013.01);
(Continued)

(58) Field of Classification Search
CPC .. G01N 21/6486; A61B 5/0059; A61B 5/1455
See application file for complete search history.

(56) References Cited

U.S. PATENT DOCUMENTS 5,525,466 A 6/1996 Slovacek et al.
6,103,535 A * 8/2000 Pilevar ............... G01N 21/6428
436/805

(Continued)

FOREIGN PATENT DOCUMENTS

EP 3163340 A1 5/2017

OTHER PUBLICATIONS

Wikipedia, "Forster Resonance Energy Transfer", Wikipedia, Available Online at, https://en.wikipedia.org/wiki/F%C3%B6rster_resonance_energy_transfer, Jul. 15, 2018, 11 pages.

(Continued)

*Primary Examiner* — Hugh Maupin
(74) *Attorney, Agent, or Firm* — Kilpatrick Townsend & Stockton LLP

(57) ABSTRACT

The disclosure provides an optical probe comprising an optical waveguide attached to a molecular switch that produces an altered optical signal upon binding a target molecule. The disclosure also provides an optical sensor system comprising an optical probe, a light source configured to emit the excitation light to be coupled into the optical waveguide of the optical probe; and a detector.

16 Claims, 27 Drawing Sheets

(52) U.S. Cl.
CPC .......... *A61B 5/6801* (2013.01); *A61B 5/6846* (2013.01); *G01N 21/648* (2013.01); *G01N 2021/6441* (2013.01); *G01N 2021/6484* (2013.01)

(56) References Cited

U.S. PATENT DOCUMENTS

| | | | |
|---|---|---|---|
| 6,974,673 B2* | 12/2005 | Lockhart | G01N 21/7703 435/7.1 |
| 7,657,133 B2 | 2/2010 | Hecht et al. | |
| 8,280,470 B2 | 10/2012 | Milner et al. | |
| 8,440,985 B2 | 5/2013 | Martinelli et al. | |
| 9,714,863 B2 | 7/2017 | Gotsmann et al. | |
| 10,835,127 B2* | 11/2020 | Peter | A61B 5/0086 |
| 2002/0135780 A1* | 9/2002 | Budach | G01N 21/6452 356/521 |
| 2005/0260677 A1* | 11/2005 | Saaski | G02B 6/4206 435/7.1 |
| 2009/0034902 A1* | 2/2009 | Izmailov | B82Y 15/00 385/12 |
| 2009/0042735 A1* | 2/2009 | Blair | C12Q 1/6816 506/9 |
| 2009/0304551 A1* | 12/2009 | Mutharasan | G01N 21/7703 422/82.11 |
| 2009/0310139 A1* | 12/2009 | Slater | G01N 21/7703 356/445 |
| 2010/0241100 A1* | 9/2010 | Blumenfeld | A61B 5/6849 600/584 |
| 2011/0281746 A1* | 11/2011 | Chagovetz | C12Q 1/6813 506/9 |
| 2014/0107495 A1 | 4/2014 | Marinelli et al. | |

OTHER PUBLICATIONS

Chiavaioli et al., "Biosensing With Optical Fiber Gratings", Nanophotonics, vol. 6, Issue 4, 2017, pp. 663-679.

PCT/US2019/057728, "International Search Report and Written Opinion", dated Jan. 16, 2020, 16 pages.

Tyagi et al., "Molecular Beacons: Probes that Fluoresce Upon Hybridization", Nature Biotechnology, vol. 14, Mar. 1996, pp. 303-308.

* cited by examiner

OPTICAL REAL-TIME BIOSENSOR

CROSS-REFERENCES TO RELATED APPLICATIONS

This application is a 371 application and claims the benefit of PCT Application No. PCT/US2019/057728, filed Oct. 23, 2019, which claims the benefit of priority to U.S. Provisional Application No. 62/750,056, filed Oct. 24, 2018, entitled "OPTICAL REAL-TIME BIOSENSOR," the entire contents of which are incorporated herein by reference for all purposes.

STATEMENT AS TO RIGHTS TO INVENTIONS MADE UNDER FEDERALLY SPONSORED RESEARCH AND DEVELOPMENT

This invention was made with Government support under contract no. OD025342 awarded by the National Institutes of Health. The Government has certain rights in the invention.

BACKGROUND

Existing biosensor technology for the continuous measurement of specific biomolecules in vivo may be limited to a handful of molecules, such as blood, oxygen and glucose. These sensors rely on biochemical features of the biomarker to achieve real-time detection, and thus may be difficult to be generalized to other molecules. For measuring other biomarkers in vivo, current tools may lack the necessary chemical specificity, detection sensitivity, spatial resolution, and temporal resolution.

SUMMARY

In some aspects, an optical probe is provided. In some embodiments, the optical probe comprises: an optical waveguide configured to propagate an excitation light; one or more molecular switches attached to a surface of the optical waveguide, either at the end facet or along one or more side wall of the optical waveguide each molecular switch configured to change from a first conformation to a second conformation upon binding to a target molecule; and one or more optical reporters, each optical reporter attached to a respective molecular switch and configured, when exposed to the excitation light, to produce an optical signal that changes upon binding of the molecular switch to a target molecule, wherein the optical signal is transmitted through the optical waveguide.

In some embodiments, the optical probe comprises: an optical waveguide having a first end and a second end, the first end configured to receive excitation light to be propagated through the optical waveguide and to be emitted from the second end or a middle region into a surrounding medium; one or more molecular switches attached to a facet or a sidewall of the second end or the middle region of the optical waveguide, wherein the molecular switches are configured to change conformation upon binding to a corresponding target molecule; and one or more optical reporters, the optical reporters attached to a respective molecular switch and configured, when exposed to the excitation light, to produce an optical signal that changes upon binding of the respective molecular switch to the corresponding target molecule in the surrounding medium, wherein the optical signal is coupled back into the optical waveguide via the second end and propagated through the optical waveguide to be emitted from the first end or the second end. In some embodiments, the middle region of the optical waveguide can be a tapered middle region. In these embodiments, the optical signal can be propagated to an end or tip of the optical waveguide from the tapered middle region.

In some embodiments, the optical waveguide comprises an optical fiber. In some embodiments, the optical fiber comprises a multimode optical fiber. In some embodiments, the optical fiber comprises a single mode optical fiber. In some embodiments, the multimode optical fiber comprises a graded-index multimode optical fiber or a step-index multimode optical fiber.

In some embodiments, at least some of the one or more molecular switches are attached to an end facet at the tip of the optical fiber.

In some embodiments, at least some of the one or more molecular switches are attached to a side wall at the tip of the optical fiber, and the one or more optical reporters are exposed to the excitation light in an evanescent optical field in a medium surrounding the side wall. In some embodiments, the evanescent optical field extends to a distance less than one micron from the sidewall. In some embodiments, the optical signal is propagated through the optical waveguide to be emitted from the first end.

In some embodiments, at least a first molecular switch of the one or more molecular switches is attached to the sidewall of the middle region of the optical waveguide, and the respective optical reporter attached to the first molecular switch is exposed to an evanescent optical field of the excitation light adjacent the sidewall. In some embodiments, the optical signal is propagated through the optical waveguide to be emitted from the second end.

In some embodiments, the one or more optical reporters comprise one or more fluorescent labels. In some embodiments, the one or more fluorescent labels comprise a donor fluorophore and an acceptor fluorophore such that the donor fluorophore and acceptor fluorophore interact to produce a detectable difference in fluorescent signal between (i) a molecular switch conformation when the molecular switch binds the target and (ii) a molecular switch conformation when the molecular switch does not bind the target.

In some embodiments, at least a first molecular switch of the one or more molecular switches is attached to a sidewall of the second end or the middle region (e.g., a tapered middle region) of the optical waveguide, and the respective optical reporter attached to the first molecular switch is exposed to an evanescent optical field of the excitation light adjacent the sidewall. In some embodiments, the evanescent optical field extends to a distance less than one micron from the sidewall.

In some embodiments, the one or more optical reporters comprise one or more fluorescent labels. In some embodiments, the one or more fluorescent labels comprise a donor fluorophore and an acceptor fluorophore such that the donor fluorophore and acceptor fluorophore interact with each other to emit fluorescence light when the molecular switch attached thereto changes conformation. For example, the donor fluorophore and acceptor fluorophore interact to produce a detectable difference in fluorescent signal between (i) a molecular switch conformation when the molecular switch binds the target and (ii) a molecular switch conformation when the molecular switch does not bind the target.

In some embodiments, the molecular switch comprises a nucleic acid, a protein, a polymer comprising nucleic acids and proteins, or a chemically modified version thereof. The molecular switch can be a synthetic polymer, e.g., a synthetic polymer comprising nucleic acids, proteins, and/or organic small molecules. A synthetic polymer can comprise natural and/or non-natural nucleic acids and natural and/or non-natural amino acids. In some embodiments, the natural and/or non-natural nucleic acids and natural and/or non-natural amino acids in the synthetic polymer can be further modified by one or more organic small molecules, e.g., a boronic acid modified uracil or other nucleotide.

In some embodiments of the optical probe, the one or more molecular switches comprise at least a first molecular switch and a second molecular switch, wherein the first molecular switch changes conformation upon binding to a first target molecule, and the second molecular switch changes conformation upon binding to a second target molecule; and the one or more optical reporters comprise at least a first optical reporter and a second optical reporter, wherein the first optical reporter is attached to the first molecular switch and configured to produce a first optical signal in a first wavelength range upon binding to the first target molecule, and the second optical reporter is attached to the second molecular switch and configured to produce a second optical signal in a second wavelength range different from the first wavelength range upon binding to the second target molecule.

In some aspects, an optical sensor system is provided. In some embodiments, the system comprises: a light source for emitting an excitation light; the optical probe as described above or elsewhere herein; and a photodetector configured to (i) receive the optical signals produced by the one or more optical reporters as transmitted through the waveguide and (ii) detect change of the optical signals, thereby allowing for detection of a concentration of the target molecule.

In some embodiments, the system comprises: the optical probe as described above; a light source configured to emit the excitation light to be coupled into the optical waveguide of the optical probe; a detector configured to (i) receive the optical signals produced by the one or more optical reporters that are transmitted through the optical waveguide, and (ii) detect changes of the optical signals, thereby allowing for detection of a concentration of the corresponding target molecule.

In some embodiments, the excitation light is in a first wavelength range, and the optical signals produced by the one or more optical reporters are in a second wavelength range different from the first wavelength range, and the optical sensor system further comprising an optical filter for transmitting the optical signals in the second wavelength range and blocking the excitation light in the first wavelength range. In some embodiments, the optical filter comprises an optical spectrometer.

In some embodiments, the excitation light is in a first wavelength range, wherein the optical signals produced by the one or more optical reporters are in a second wavelength range different from the first wavelength range, and the detector comprises an optical spectrometer. In some embodiments, the detector comprises a single photon counting module (SPCM). In certain embodiments, a power of the excitation light emitted by the light source ranges from about 1 nW to about 300 nW, or from about 10 nW to about 200 nW, or from about 40 nW to about 150 nW, or from about 50 nW to about 100 nW (e.g., about 1 nW to about 280 nW, about 1 nW to about 260 nW, about 1 nW to about 240 nW, about 1 nW to about 220 nW, about 1 nW to about 200 nW, about 1 nW to about 180 nW, about 1 nW to about 160 nW, about 1 nW to about 140 nW, about 1 nW to about 120 nW, about 1 nW to about 100 nW, about 1 nW to about 80 nW, about 1 nW to about 60 nW, about 1 nW to about 40 nW, about 1 nW to about 20 nW, or about 1 nW to about 10 nW; e.g., about 1 nW, 5 nW, 10 nW, 20 nW, 30 nW, 40 nW, 50 nW, 60 nW, 70 nW, 80 nW, 90 nW, 100 nW, 110 nW, 120 nW, 130 nW, 140 nW, 150 nW, 160 nW, 170 nW, 180 nW, 190 nW, 200 nW, 210 nW, 220 nW, 230 nW, 240 nW, 250 nW, 260 nW, 270 nW, 280 nW, 290 nW, or 300 nW). In certain embodiments, a power of the excitation light emitted by the light source ranges from about 300 nW to about 3 µW, or from 500 nW to about 2.5 µW, or from 1 µW to about 2 µW, or from 1.5 µW to about 2 µW (e.g., about 500 nW to about 3 µW, about 700 nW to about 3 µW, about 900 nW to about 3 µW, about 1 µW to about 3 µW, about 1.2 µW to about 3 µW, about 1.4 µW to about 3 µW, about 1.6 µW to about 3 µW, about 1.8 µW to about 3 µW, about 2 µW to about 3 µW, about 2.2 µW to about 3 µW, about 2.4 µW to about 3 µW, about 2.6 µW to about 3 µW, about 2.8 µW to about 3 µW, about 300 nW to about 2.8 µW, about 300 nW to about 2.6 µW, about 300 nW to about 2.4 µW, about 300 nW to about 2.2 µW, about 300 nW to about 2 µW, about 300 nW to about 1.8 µW, about 300 nW to about 1.6 µW, about 300 nW to about 1.4 µW, about 300 nW to about 1.2 µW, about 300 nW to about 1 µW, about 300 nW to about 800 nW, or about 300 nW to about 600 nW).

In some embodiments, anti-fade solutions or oxygen scavengers can be added to reduce photobleaching.

In some embodiments of the optical sensor system, the optical probe further comprises a tube surrounding the second end of the optical waveguide, the tube being configured to protect the second end of the optical waveguide when inserted into a sample.

In some embodiments of the optical sensor system, the optical sensor system is wearable or implantable in the living subject (e.g., an animal or a human).

In some embodiments, the system comprises plurality of multiple optical probes, e.g., one, two, three, four, or five or more optical probes that bind different targets, each optical probe being provided in a number of copies. In some embodiments, the system comprises at least a first optical probe and a second optical probe, wherein the first optical probe comprises: a first optical waveguide having a first end and a second end, the first end configured to receive excitation light to be propagated through the first optical waveguide and to be emitted from the second end or a middle region into a surrounding medium; one or more first molecular switches attached to a facet or a sidewall of the second end or the middle region of the optical waveguide, wherein the first molecular switches are configured to change conformation upon binding to a corresponding first target molecule; and one or more first optical reporters, the first optical reporters attached to a respective molecular switch and configured, when exposed to the excitation light, to produce a first optical signal change upon binding of the respective molecular switch to the corresponding first target molecule in the surrounding medium, wherein the first optical signal is coupled back into the optical waveguide via the second end and propagated through the optical waveguide to be emitted from the first end or the second end; and the second optical probe comprises: a second optical waveguide having a first end and a second end, the first end configured to receive excitation light to be propagated through the second optical waveguide and to be emitted from the second end or a middle region into a surrounding medium; one or more second molecular switches attached to a facet or a sidewall of the second end or the middle region of the second optical waveguide, wherein the second molecular switches are configured to change conformation upon binding to a corresponding second target molecule; and one or more second optical reporters, the second optical reporters attached to a respective molecular switch and configured, when exposed to the excitation light, to produce a second optical signal change upon binding of the respective molecular switch to the corresponding second target molecule in the surrounding medium, wherein the second optical signal is coupled back into the optical waveguide via the second end and propagated through the second optical waveguide to be emitted from the first end or the second end.

In some embodiments, the sample is an in vivo sample (e.g., an in vivo tissue) of a living subject (e.g., an animal or a human), and the optical sensor system further comprises: means for administering an amount of an agent to the living subject; and a feedback control mechanism configured to adjust the amount of the agent based on the detected concentration of the target molecule in the sample as measured by the optical probe.

In some embodiments, the sample is an in vivo sample (e.g., an in vivo tissue) of a living subject (e.g., an animal or a human), and the optical sensor system is wearable or implantable in the living animal.

In some aspects, a method of detection of a target molecule in a sample is provided. In some embodiments, the method uses the optical sensor system described above. In some embodiments, the method comprises: contacting the one or more molecular switches of the optical probe as described above or elsewhere herein to the sample; emitting the excitation light from the light source; and measuring, using the detector, changes of the optical signals, thereby detecting a concentration of the target molecule in the sample.

In some embodiments, the sample is an in vivo sample (e.g., an in vivo tissue) of a living subject (e.g., an animal or a human), and the measuring is performed continuously. In some embodiments, the method further comprises: administering an amount of an agent to the living subject; and adjusting the amount of the agent based on the detected concentration of the target molecule in the sample. In some embodiments, the adjusting is determined by a feedback control mechanism configured to adjust the amount of the agent based on the detected concentration of the target molecule in the sample as measured by the optical sensor system. In other embodiments, the method can be used to measure target molecules that are released naturally in the sample by the subject.

In some embodiments, the measuring is performed in a ratiometric manner. In some embodiments, the optical reporters comprise a donor fluorophore and an acceptor fluorophore, wherein the measuring comprises measuring a first optical signal at the emission wavelength of the donor fluorophore and a second optical signal at the emission wavelength of the acceptor fluorophore, and wherein the first optical signal and the second optical signal are at different levels when the molecular switch is not bound to the target molecule compared to when the molecular switch is bound to the target molecule. In certain embodiments, the first optical signal is higher than the second optical signal. In other embodiments, the first optical signal is lower than the second optical signal.

In some embodiments, when the molecular switch is bound to the target molecule, the donor fluorophore and the acceptor are in proximity of each other to produce a FRET signal. In other embodiments, when the molecular switch is not bound to the target molecule, the donor fluorophore and the acceptor are in proximity of each other to produce a FRET signal.

In some embodiments, the method first comprises generating a ratio of the first optical signal and the second optical signal.

In some aspects, a method of detection of a target molecule in a sample is provided. In some embodiments, the method comprises: contacting the one or more molecular switches of the optical probe as described above or elsewhere herein to the sample; propagating the excitation light in the core of the optical waveguide of the optical probe; receiving at a photodetector the optical signal from the one or more molecular switches as transmitted through the optical waveguide; and measuring a change of the optical signals, thereby detecting a concentration of the target molecule in the sample.

In some embodiments, the sample is an in vivo sample of a living animal (including but not limited to a human) and the measuring is performed continuously. In some embodiments, the method further comprises: administering an amount of an agent to the living animal; and adjusting the amount of the agent based on the detected concentration of the target molecule in the sample. In some embodiments, the adjusting is determined by a feedback control mechanism configured to adjust the amount of the agent based on the detected concentration of the target molecule in the sample as measured by the optical probe.

DEFINITIONS

Figure 1:
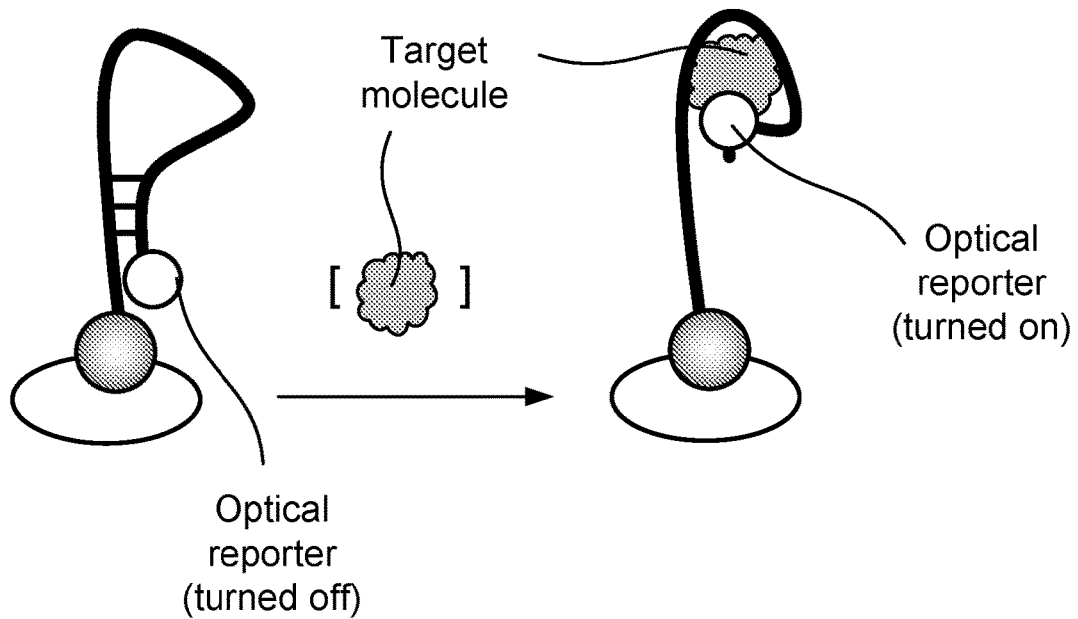
FIG. 1 illustrates schematically an aptamer that changes its conformation upon binding to a target molecule according to some embodiments.

The terms "label" and "detectable label" may be used interchangeably herein to refer to a molecule capable of detection, including, but not limited to, radioactive isotopes, fluorophores, quantum dots, nanoparticles (e.g., fluorescent nanoparticles), chemiluminescers, chromophores, enzymes, enzyme substrates, enzyme cofactors, enzyme inhibitors, chromophores, dyes, metal ions, metal sols, ligands (e.g., biotin, avidin, streptavidin or haptens) and the like. Exemplary detectable moieties suitable for use as detectable labels include affinity tags and fluorescent proteins. "Optical reporters" as used herein can include, for example, fluorescent dyes or other fluorescent molecules as well as other molecules that can produce an optical signal (e.g., light) that can be transmitted through a waveguide.

As used herein the term "aptamer" or "aptamer sequence" refers to a nucleic acid having a specific binding affinity for a target, e.g., a target molecule, wherein such target is other than a polynucleotide that binds to the aptamer or aptamer sequence through a mechanism which predominantly depends on Watson/Crick base pairing.

The terms "nucleic acid", "nucleic acid sequence", "nucleic acid molecule" and "polynucleotide" may be used interchangeably herein and refer to a polymeric form of nucleotides of any length, either deoxyribonucleotides or ribonucleotides, or analogs thereof, and may include naturally occurring nucleotides and/or modified (e.g., non-natural) nucleotides. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular. In some embodiments, nucleic acids (e.g., natural and non-natural nucleic acids) can be chemically modified with one or more organic small molecules, e.g., boronic acid modified nucleic acids. Examples of modified nucleic acids can be found in, but are not limited to, those in, e.g., Gordon et al., *ACS Chem Biol.* Oct. 12, 2019; Meek et al., *Methods.* 106:29-36, 2016; and Chen et al., *Bioorg Med Chem Lett.* 26(16):3958-62, 2016).

As used herein, the term "oligonucleotide" can refer to a polynucleotide chain, including but not limited to those less than 200 residues long, most typically between 15 and 100 nucleotides long, but also intended to encompass longer polynucleotide chains. Oligonucleotides can be single- or double-stranded.

As used herein, the term "molecular switch" refers to a probe molecule capable of binding a target molecule, wherein the binding of the target molecule causes a change in conformation of the molecular switch that is detectable. Non limiting examples of a molecular switch are aptamers, antibodies, peptides, or other molecules that change conformation upon binding to a target molecule. In some embodiments, the molecular switch has a first conformation when bound to the target and a second conformation when not bound to the target, wherein one or both of the first conformation and the second conformation provides a detectable signal. In some embodiments, a change from one conformation to a second conformation results in a change in optical signal. Conformation switching probes may be reversible or non-reversible.

The terms "peptide", "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, .beta.-galactosidase, luciferase, etc.; and the like.

The term "sequence" as used, for example, in the context of an aptamer sequence, a nucleic acid sequence or an amino acid sequence may refer to the primary structure, e.g., the order of monomeric subunits, e.g., nucleotides or amino acids, and/or to the molecule having the primary structure.

The terms "antibody" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins including an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. Also encompassed by the terms are Fab', Fv, F(ab')2, and other antibody fragments that retain specific binding to antigen.

Antibodies may exist in a variety of other forms including, for example, Fv, Fab, and (Fab')$_2$, as well as bi-functional (i.e. bi-specific) hybrid antibodies (e.g., Lanzavecchia et al., *Eur. J. Immunol.* 17, 105 (1987)) and in single chains (e.g., Huston et al., *Proc. Natl. Acad. Sci. U.S.A.*, 85, 5879-5883 (1988) and Bird et al., *Science*, 242, 423-426 (1988), which are incorporated herein by reference). (See, generally, Hood et al., *Immunology*, Benjamin, N.Y., 2nd ed. (1984), and Hunkapiller and Hood, *Nature*, 323, 15-16 (1986).

DETAILED DESCRIPTION

Embodiments of the present invention provide an optical probe that can be used as a biosensor that can continuously detect specific biomolecules with high sensitivity, specificity, and stability in real-time. In some embodiments, the biosensor can continuously measure the physiological concentration of multiple analytes in live subjects. In other embodiments, the biosensor can provide end-point measurements of specific biomolecules. The optical probe comprises an optical waveguide that can transmit light. The optical waveguide is made up of a core or a core and a cladding. A plurality of molecular switches is attached to a surface of the optical waveguide (e.g., near or at the tip of the optical waveguide or in a tapered middle of the optical waveguide).

I. OPTICAL PROBE

According to some embodiments, an optical probe is used as a biosensor. The optical probe may include an optical waveguide configured to propagate an excitation light, and transmit an optical signal from optical reporters on the optical switches to a photodetector. The optical probe also includes molecular switches attached to the surface of the optical waveguide and configured to change its molecular conformation upon binding to a target molecule. The optical probe includes optical reporters attached to the molecular switches and configured to, when exposed to the excitation light, produce an optical signal change when the molecular switch binds a target molecule compared to when the molecular switch does not bind the target molecule. This can be manifested, for example, by a change of conformation of the molecular switch when bound to the target molecule compared to its unbound state. The optical signal change is propagated through the optical waveguide to a photodetector. Intensity of the change of signal from a plurality of molecular switches can be used to determine concentration of the target molecule in a sample, including but not limited to in vivo.

A. Molecular Switches and Optical Reporters

In some embodiments, the molecular switches are engineered with optical reporters. One non-limiting implementation of the molecular switch includes optical reporters that comprise intra-chain fluorophore donor/acceptor pair such that they generate a fluorescent signal upon binding the target via Förster (or fluorescence) resonance energy transfer (FRET). The fluorescence intensity generated from a plurality of molecular switches attached to a waveguide can be proportional to the amount of target bound to the aptamers, which enables quantitative measurements. FRET is a process by which radiationless transfer of energy occurs from an excited state fluorophore to a second chromophore in close proximity. The range over which the energy transfer can take place is limited to approximately 10 nanometers (100 angstroms), and the efficiency of transfer is extremely sensitive to the separation distance between fluorophores. Thus, as used herein, the term "FRET" refers to a physical phenomenon involving a donor fluorophore and a matching acceptor fluorophore selected so that the emission spectrum of the donor overlaps the excitation spectrum of the acceptor, and further selected so that when donor and acceptor are in close proximity (usually 10 nm or less), excitation of the donor will cause excitation of and emission from the acceptor, as some of the energy passes from donor to acceptor via a quantum coupling effect. Thus, a FRET signal serves as a proximity gauge of the donor and acceptor; only when they are in close proximity is a signal generated. The FRET donor moiety (e.g., donor fluorophore) and FRET acceptor moiety (e.g., acceptor fluorophore) are collectively referred to herein as a "FRET pair". For example, in some embodiments, the molecular switch brings the donor and acceptor into close proximity upon binding of a target molecule but not when the target is absent. Alternatively, in some embodiments, the molecular switch brings the donor and acceptor into close proximity when the target molecule is absent and not upon binding of a target molecule. In some embodiments, the donor fluorophore and the acceptor fluorophore in a FRET pair are chosen such that the excitation wavelength of the donor fluorophore and the excitation wavelength of the acceptor fluorophore are sufficiently different from each other such that detection of one does not significantly (e.g., greater than 5 or 10%) affect detection of the other. This reduces false positive signals that might otherwise occur from detection of the two fluorophores. For example, the excitation wavelength of the one of the fluorophores can be in the blue wavelength range (e.g., between 450 nm and 495 nm, 450 nm and 490 nm, 450 nm and 480 nm, 450 nm and 470 nm, 450 nm and 460 nm, 460 nm and 495 nm, 470 nm and 495 nm, 480 nm and 495 nm, or 490 nm and 495 nm), and the excitation wavelength of the other fluorophore can be in the green wavelength range (e.g., between 500 nm and 570 nm, 500 nm and 560 nm, 500 nm and 550 nm, 500 nm and 540 nm, 500 nm and 530 nm, 500 nm and 520 nm, 500 nm and 510 nm, 510 nm and 570 nm, 520 nm and 570 nm, 530 nm and 570 nm, 540 nm and 570 nm, 550 nm and 570 nm, or 560 nm and 570 nm). Exemplary FRET donors include but are not limited to fluorescent dyes such as xanthene dyes (for example, Pvhodamine, fluorescein), naphthalimides, coumarins, cyanine dyes, oxazines, pyrenes, porphyrins, and acridines. Exemplary FRET pairs can be found in, for example, U.S. Pat. No. 8,124,357 and US Patent Publication 2018/0142222. Selection of FRET pairs is described in, e.g., Bajar et al., *Sensors* 2016, 16, 1488. Exemplary FRET acceptors can be a red-shifted dye or a dark quencher (i.e., a quencher that dissipates energy into heat). In yet other embodiments, the labels on the molecular switch can interact via static quenching or Dexter quenching.

Structure-switching reagents can be aptamers, or other reagents such as engineered antibodies that are made to switch and provide an optical signal upon binding. This disclosure is not necessarily limited to particular molecular switches. Exemplary aptamer structures are described in, e.g., Szostak, J. W. "In vitro selection of RNA molecules that bind specific ligands. *Nature* (1990); Gold L. et al., "Systematic evolution of ligands by exponential enrichment: RNA ligands to bacteriophage T4 DNA polymerase." *Science* (1990); Jayasena, S. D. "Aptamers: an emerging class of molecules that rival antibodies in diagnostics." *Clin. Chem.* (1999); and H. & van der Oost, J. Alternative affinity tools: more attractive than antibodies. *Biochem. J.* (2011). In the context of aptamers, a variety of library architectures have been presented in the literature for generating aptamers that change conformation upon binding to a target (e.g., D. P. Morse, *Biochem. Biophys. Res. Commun.*, vol. 359, pp. 94-101, 2007; S. G. Trevino and M. Levy, *Chembiochem*, vol. 15, no. 13, pp. 1877-81, September 2014; R. Stoltenburg, N. Nikolaus, and B. Strehlitz, *J. Anal. Methods Chem.*, vol. 2012, 2012; F. Pfeiffer and G. Mayer, *Front. Chem.*, vol. 4, no. June, pp. 1-21, 2016; Ruscito et al., *Front. Chem.* 4:14 (2016); Yingfu Li et al.; JACS (2003); H. T. Soh et. al. PNAS (2010); Weihong Tan et al. JACS (2008); Stanton M. et. al. Analytical Biochemistry, (2001), WO2014100434. A suitable method for generating an aptamer is with the process entitled "Systematic Evolution of Ligands by Exponential Enrichment" ("SELEX") generally described in, e.g., U.S. Pat. No. 5,475,096 entitled "Nucleic Acid Ligands", and U.S. Pat. No. 5,270,163 (see also WO 91/19813) entitled "Nucleic Acid Ligands".

In some embodiments, the aptamer can include a nucleic acid, a protein, a polymer comprising nucleic acids and proteins, or a chemically modified version thereof. The aptamer can be a synthetic polymer, e.g., a synthetic polymer comprising nucleic acids, proteins, and/or organic small molecules. A synthetic polymer can comprise natural and/or non-natural nucleic acids and natural and/or non-natural amino acids. In some embodiments, the natural and/or non-natural nucleic acids and natural and/or non-natural amino acids in the synthetic polymer can be further modified by one or more organic small molecules, e.g., a boronic acid modified uracil or other nucleotide.

In some embodiments, the aptamer can include a non-natural nucleotide. A non-natural nucleotide may contain a modification to either the base, sugar, or phosphate moiety compared to a naturally occurring nucleotide. A modification may be a chemical modification. Modifications may be, for example, of the 3'OH or 5'OH group of the backbone, of the sugar component, or of the nucleotide base. In some embodiments, the nucleotide is an unnatural nucleoside triphosphate. In some embodiments, one or more of the 4 naturally-occurring nucleotides (A, G, C, T/U) are replaced with a non-natural nucleotide. In some embodiments, two, three, or all four naturally-occurring nucleotides can be replaced by different non-natural nucleotides.

In some embodiments, a non-natural nucleotide may contain modifications to the nucleotide base. A modified base is a base other than the naturally occurring adenine, guanine, cytosine, thymine, or uracil. Examples of modified bases include, but are not limited to, C8-alkyne-uracil, uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifiuoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Examples of non-natural nucleotides include, but are not limited to, 5-substituted pyrimidines, 6-azapyrimidines and N-2 substituted purines, N-6 substituted purines, 0-6 substituted purines, 2-aminopropyladenine, 5-propynyluracil, 5-propynylcytosine, 5-methylcytosine, fluorinated nucleic acids, 5-substituted pyrimidines, 6-azapyrimidines and N-2, N-6 and O-6 substituted purines, including 2-aminopropyladenine, 5-propynyluracil and 5-propynylcytosine, 5-methylcytosine (5-me-C), 5-hydroxymethyl cytosine, xanthine, hypoxanthine, 2-aminoadenine, 6-methyl other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyl adenine, 2-F-adenine, 2-amino-adenine, 8-azaguanine, 8-azaadenine, 7-deazaguanine, 7-deazaadenine, 3-deazaguanine, 3-deazaadenine, tricyclic pyrimidines, phenoxazine cytidine ([5,4-b][1,4]benzoxazin-2(3H)-one), phenothiazine cytidine (1H-pyrimido[5,4-b][1,4]benzothiazin-2(3H)-one), phenoxazine cytidine (e.g., 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, 5-iodouracil, 2-amino-adenine, 6-thio-guanine, 2-thio-thymine, 4-thio-thymine, 5-propynyl-uracil, 4-thio-uracil, N4-ethylcytosine, 7-deazaguanine, 7-deaza-8-azaguanine, 5-hydroxycytosine, 2'-deoxyuridine, and 2-amino-2'-deoxyadenosine. Examples of other synthetic nucleotides may be found in, e.g., Malyshev *Nature.* 509(7500):385, 2014.

FIG. 1 illustrates schematically an aptamer that changes its conformation upon binding to a target molecule according to some embodiments. As depicted, an optical reporter (e.g., a fluorescence label) is attached to the aptamer, and is configured to produce fluorescence signals when the aptamer binds to the target molecule (referred to as being "turned on.").

One can select a known molecular switch or one can be designed. Design of molecular switches can involve selection or identification of a molecule that binds the target. For example, a large number of aptamers are known that bind to targets. As described in the Examples, one can begin with such aptamers and then alter the aptamer to convert it into a conformation molecular switch. For example, a stem-loop structure can be formed with respective members of a FRET pair attached at the two termini of the aptamer strand, using an intervening DNA sequence (for example, polyT) as a linker. In this construct, a short DNA competitor hybridizes with a partial section of the aptamer sequence (see FIG. 19), keeping the fluorophore and quencher of the FRET pair in close proximity (signal-off) but allowing dehybridization when aptamer binds to the target molecule, and moving the quencher away from the fluorophore (signal-on). By optimizing both the length of the stem and linker strands, one can tune the responsiveness/characteristics of the aptamer-switch. Once the aptamer-switch is created, the fluorophore-quencher can be readily substituted with a FRET pair for ratiometric fluorescence signal detection.

B. Optical Waveguides

As noted above, the molecular switch is attached (covalently or non-covalently linked) to the surface of an optical waveguide (e.g., the surface of the core or the surface of the cladding). An optical waveguide is a physical structure that guides electromagnetic waves in the optical spectrum. Optical waveguides can be classified according to their geometry (e.g., planar, strip, or fiber waveguides), mode structure (e.g., single-mode, multimode), refractive index distribution (e.g., step or gradient index), and material (e.g., glass, polymer, semiconductor). An optical waveguide may include a core and a cladding, which may be surrounded by a medium (e.g., air or liquid). In some embodiments, light may be confined in the core by total internal reflection, which can occur if the index of refraction of the core is greater than that of the cladding or the surrounding medium. In some embodiments, an optical waveguide can be a fiber that has an angle polished connector. The angle polished connector can have an angle that is between 5° and 15° (e.g., between 5° and 13°, between 5° and 11°, between 5° and 9°, between 5° and 7°, between 7° and 15°, between 9° and 15°, between 11° and 15°, or between 13° and 15°; e.g., 6°, 7°, 8°, 9°, 10°, 11°, 12°, 13°, 14°, or 15°, 5°) which minimizes back reflection. In some embodiments, the optical waveguide can be protected by a tube (e.g., a capillary tube). For example, the second end of the optical waveguide can be surrounded by a tube (e.g., a capillary tube), which can protect the optical waveguide when it is inserted into the sample.

In some embodiments, the wave guide is an optical fiber. An optical fiber is a flexible, transparent fiber made by drawing glass (silica) or plastic to a small diameter (e.g., a diameter slightly thicker than that of a human hair). Optical fibers are used most often as a means to transmit light between the two ends of the fiber. Optical fibers typically include a core surrounded by a transparent cladding material with a lower index of refraction. Light is kept in the core by the phenomenon of total internal reflection which causes the fiber to act as a waveguide. Optical fibers that support many propagation paths or transverse modes are called multimode fibers, while those that support a single mode are called single-mode fibers (SMF). Multimode fibers generally have a wider core diameter (e.g., up to about 100 µm; e.g., between 10 µm and 100 µm, 10 µm and 90 µm, 10 µm and 80 µm, 10 µm and 70 µm, 10 µm and 60 µm, 10 µm and 50 µm, 10 µm and 40 µm, 10 µm and 30 µm, or 10 µm and 20 µm). Single-mode fibers may have core diameters less than about ten times the wavelength of the propagating light, and are designed to carry light only directly down the fiber—the transverse mode.

The materials for the optical fiber core may include for example silica, fluorozirconate, fluoroaluminate, and chalcogenide glasses, as well as crystalline materials such as sapphire. Silica and fluoride glasses usually have refractive indices of about 1.5, but some materials such as the chalcogenides can have indices as high as 3. Plastic optical fibers (POF) are commonly step-index multi-mode fibers with a core diameter of 0.5 millimeters or larger.

Step-index optical fibers have a core with a substantially homogenous refractive index profile across a diameter of the core. Graded-index optical fibers have a core with a refractive index profile that decreases with increasing radial distance from the optical axis of the fiber. Because parts of the core closer to the fiber axis have a higher refractive index than the parts near the cladding, light rays follow sinusoidal paths down the fiber. Multi-mode optical fibers can be built with either graded index or step index.

An evanescent field, or evanescent wave, is an oscillating electromagnetic field that does not propagate as an electromagnetic wave but whose energy is spatially concentrated in the vicinity of the source. An evanescent field can exist at an interface between a core of a waveguide and a cladding or between a cladding and a surrounding medium. Under total internal reflection conditions, there may be an exponentially decaying transmitted wave at the interface. This is because Maxwell's equations in a dielectric medium impose a boundary condition of continuity for certain components of the electric and magnetic fields. The exponentially decaying transmitted wave may be referred to as an evanescent field. The evanescent field created by total internal reflection may be used for near-field sensing by excite fluorophores close to a surface. For example, a decaying length of an evanescent field created by total internal reflection may range from a few tens of nanometers to a few hundreds of nanometers.

C. Optical Probes Utilizing Waveguides and Molecular Switches

According to some embodiments, the optical probe may be configured to achieve the following characteristics for implementing in clinical settings: (1) real-time continuous monitoring; (2) high sensitivity; (3) high spatial and temporal resolution; (4) simultaneous multi-analyte detection; (5) long term stability in in vivo environment.

To achieve these characteristics, an optical probe may utilize an optical waveguide (e.g., an optical fiber, or a similar device) with a surrounding optical field (e.g., an evanescent optical field). The optical waveguide may permit reliable spectroscopic measurement of chemical binding events from the tip of the optical waveguide, by conveying excitation light and detecting returning optical signals from the molecular switch, e.g., reflection or fluorescent emission. By combining the waveguide platform with the structure switching reagents, continuous tracking of rising and falling concentrations of multiple analytes in real-time and with high sensitivity may be possible.

Figure 2:
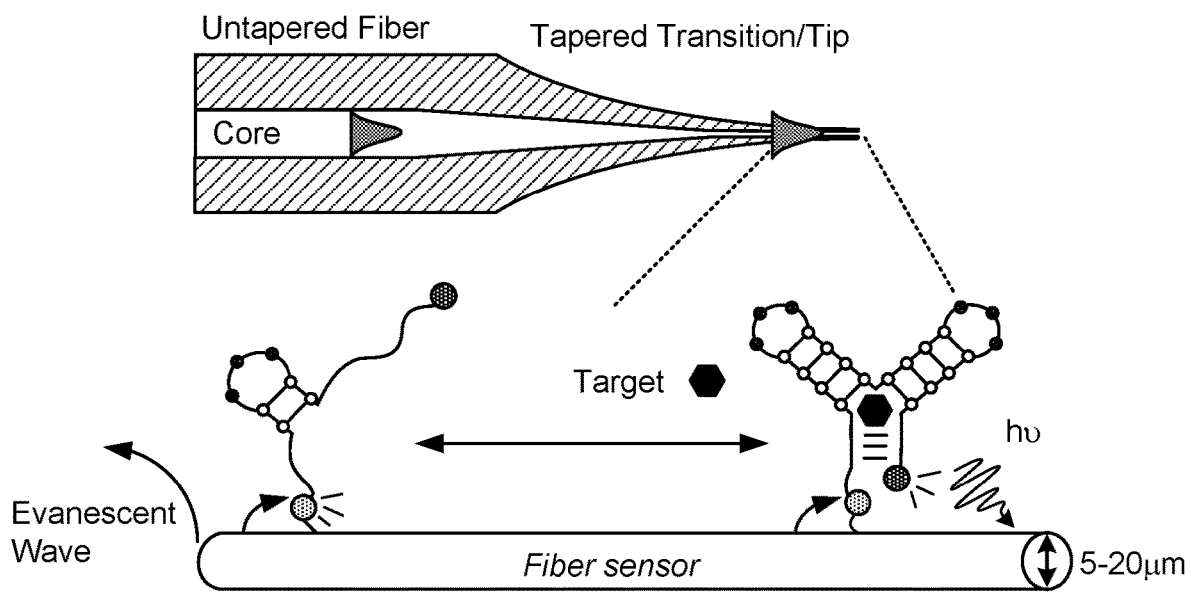
FIG. 2 illustrates schematically a waveguide with an optionally tapered tip, to which structure-switching reagents may be attached according to some embodiments.
Figure 3:
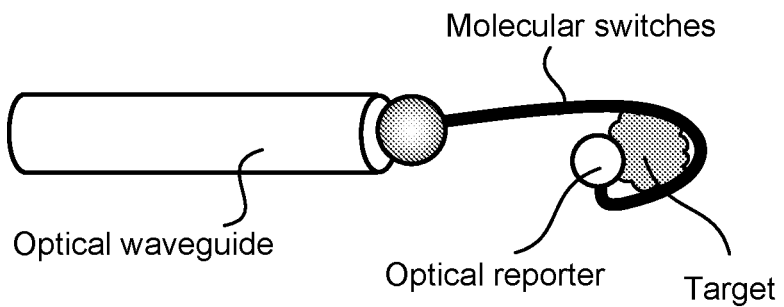
FIG. 3 illustrates schematically an optical probe according to some embodiments.

FIGS. 2 and 3 illustrate schematically some exemplary optical probes according to some embodiments. An optical probe includes an optical waveguide (e.g., an optical fiber). The optical waveguide has a core and a cladding. The core may be configured to propagate an excitation light. In some embodiments, the tip of the optical waveguide may be tapered, as illustrated in FIG. 2. In some embodiments, the cladding may be optionally removed at a portion of the tip. The optical probe also includes molecular switches attached to the tip of the optical waveguide (e.g., at a sidewall of the optical waveguide as illustrated in FIG. 2, and/or at an end facet of the optical waveguide as illustrated in FIG. 3). In some embodiments, the molecular switch is configured to change its molecular conformation upon binding to a target molecule. The optical probe also includes optical reporters (e.g., fluorescent labels, optionally FRET pairs) attached to the molecular switches. The optical reporters are configured to, when exposed to the evanescent optical field of the excitation light, produce an optical signal that changes upon the molecular switch changing its molecular conformation. The changes in the optical signals can be measured using photodetectors. In some embodiments, the power of the excitation light emitted by the light source is low in order to reduce photobleaching. In some embodiments, a power of the excitation light emitted by the light source ranges from about 1 nW to about 300 nW, or from about 10 nW to about 200 nW, or from about 40 nW to about 150 nW, or from about 50 nW to about 100 nW (e.g., about 1 nW to about 280 nW, about 1 nW to about 260 nW, about 1 nW to about 240 nW, about 1 nW to about 220 nW, about 1 nW to about 200 nW, about 1 nW to about 180 nW, about 1 nW to about 160 nW, about 1 nW to about 140 nW, about 1 nW to about 120 nW, about 1 nW to about 100 nW, about 1 nW to about 80 nW, about 1 nW to about 60 nW, about 1 nW to about 40 nW, about 1 nW to about 20 nW, or about 1 nW to about 10 nW; e.g., about 1 nW, 5 nW, 10 nW, 20 nW, 30 nW, 40 nW, 50 nW, 60 nW, 70 nW, 80 nW, 90 nW, 100 nW, 110 nW, 120 nW, 130 nW, 140 nW, 150 nW, 160 nW, 170 nW, 180 nW, 190 nW, 200 nW, 210 nW, 220 nW, 230 nW, 240 nW, 250 nW, 260 nW, 270 nW, 280 nW, 290 nW, or 300 nW). In certain embodiments, a power of the excitation light emitted by the light source ranges from about 300 nW to about 3 $\mu$W, or from 500 nW to about 2.5 $\mu$W, or from 1 $\mu$W to about 2 $\mu$W, or from 1.5 $\mu$W to about 2 $\mu$W (e.g., about 500 nW to about 3 $\mu$W, about 700 nW to about 3 $\mu$W, about 900 nW to about 3 $\mu$W, about 1 $\mu$W to about 3 $\mu$W, about 1.2 $\mu$W to about 3 $\mu$W, about 1.4 $\mu$W to about 3 $\mu$W, about 1.6 $\mu$W to about 3 $\mu$W, about 1.8 $\mu$W to about 3 $\mu$W, about 2 $\mu$W to about 3 $\mu$W, about 2.2 $\mu$W to about 3 $\mu$W, about 2.4 $\mu$W to about 3 $\mu$W, about 2.6 $\mu$W to about 3 $\mu$W, about 2.8 $\mu$W to about 3 $\mu$W, about 300 nW to about 2.8 $\mu$W, about 300 nW to about 2.6 $\mu$W, about 300 nW to about 2.4 $\mu$W, about 300 nW to about 2.2 $\mu$W, about 300 nW to about 2 $\mu$W, about 300 nW to about 1.8 $\mu$W, about 300 nW to about 1.6 $\mu$W, about 300 nW to about 1.4 $\mu$W, about 300 nW to about 1.2 $\mu$W, about 300 nW to about 1 $\mu$W, about 300 nW to about 800 nW, or about 300 nW to about 600 nW).

In some embodiments, the molecular switch can be embedded at or near the tip of an optical probe such that the tip can be inserted into a sample or animal allowing transmission of signal to and from the inserted tip outside of the sample or animal via the waveguide. In other embodiments, the molecular switch can be embedded at or near a middle region of an optical probe. In some embodiments, the middle region of the optical probe can be a tapered middle region. In these embodiments, an end of the optical probe can be configured to receive excitation light to be propagated through the optical probe and to be emitted from the tapered middle region of the optical probe and into the medium surrounding the tapered middle region. In these embodiments, the optical signal can be propagated to an end or tip of the optical probe from the tapered middle region. In these embodiments, the optical probe can form a U-shaped or V-shaped optical probe in order to insert the molecular switches, which are located in the middle region (e.g., a tapered middle region) of the optical probe, into the sample or surrounding medium for target molecule binding. In some embodiments, the optical probe exploits an evanescent wave coupling, a near-field effect that may reduce auto-fluorescent background signals. By coupling low noise and sensitive detectors with conformation changing aptamers, the optical probe can achieve simultaneous, continuous, and specific measurements of multiple biomolecules in vivo in real-time. For example, as illustrated in FIG. 2, a molecular switch may be attached to the sidewall of the optical waveguide near the end facet, where an evanescent optical field may extend thereto. Such an optical probe may be configured for minimally invasive procedures. For example, the optical probe can be inserted into the tip of a needle or syringe for insertion through the skin of an animal.

In some embodiments, multiple molecular switches may be used for probing multiple analytes simultaneously. For example, an optical probe can have at least a first molecular switch and a second molecular switch, in which the first molecular switch can change conformation upon binding to a first target molecule, and the second molecular switch can change conformation upon binding to a second target molecule. In this example, the optical probe can have at least a first optical reporter and a second optical reporter, in which the first optical reporter is attached to the first molecular switch and configured to produce a first optical signal in a first wavelength (or wavelength range) upon binding to the first target molecule, and the second optical reporter is attached to the second molecular switch and configured to produce a second optical signal in a second wavelength (or wavelength range) different from the first wavelength or wavelength range upon binding to the second target molecule.

In other embodiments, ratiometric measurements from the optical reporters can be obtained, for example to more accurately measure concentration of target molecules. In these embodiments, the optical reporters can contain a donor fluorophore and an acceptor fluorophore. The donor fluorophore and the acceptor fluorophore can be in proximity of each other to produce a FRET signal depending on the interaction of the molecular switch and the target molecule. In some embodiments, when the molecular switch is bound to the target molecule, the donor fluorophore and the acceptor are in proximity of each other to produce a FRET signal. In other embodiments, when the molecular switch is not bound to the target molecule, the donor fluorophore and the acceptor are in proximity of each other to produce a FRET signal. In ratiometric measurements, a ratio of the optical signal at the emission wavelength of the donor fluorophore and the optical signal at the emission wavelength of the acceptor fluorophore can be taken. In some embodiments, the optical signal from the donor fluorophore is higher than the optical signal from the acceptor fluorophore. In other embodiments, the optical signal from the donor fluorophore is lower than the optical signal from the acceptor fluorophore.

Figure 4:
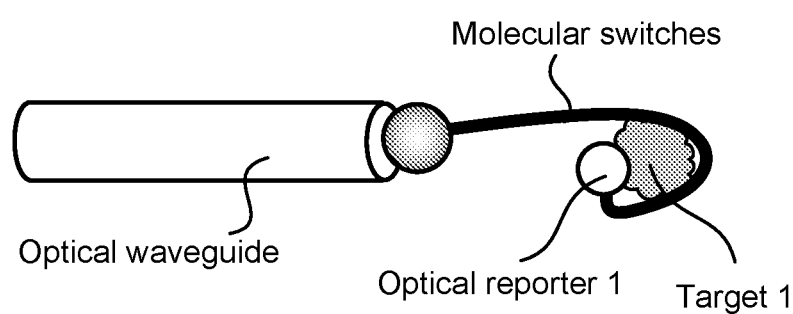
FIG. 4 illustrates schematically three types of structure-switching reagents configured to bind to three different types of target molecules, and with three different types of optical reporters attached, according to some embodiments.
Figure 4:
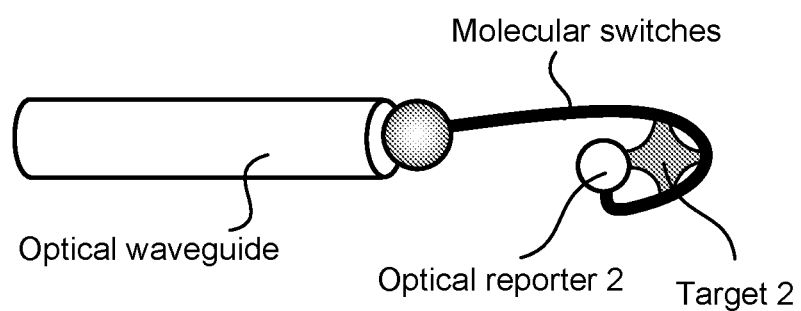
Figure 4:
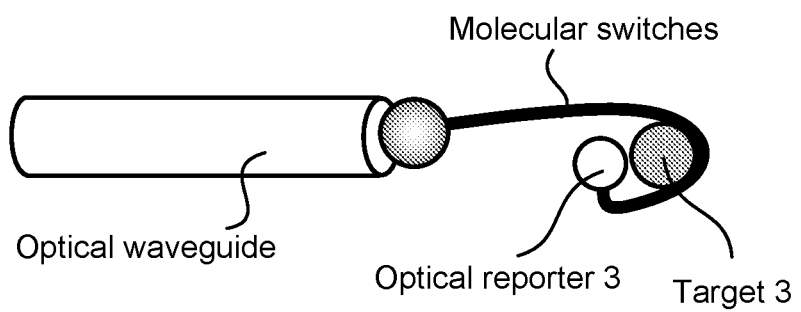
Figure 5A:
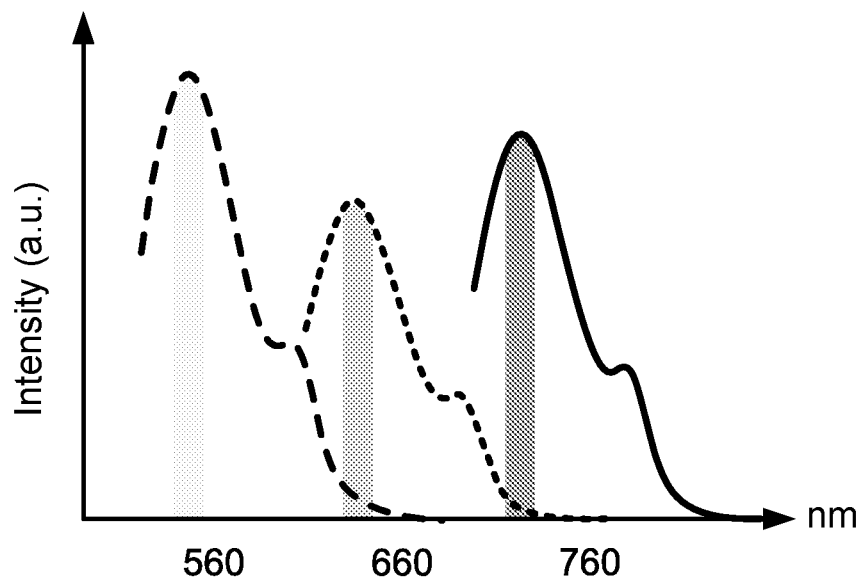
FIG. 5A illustrates schematically fluorescence spectra of the three different types of optical reporters illustrated in FIG. 4 according to some embodiments.
Figure 5B:
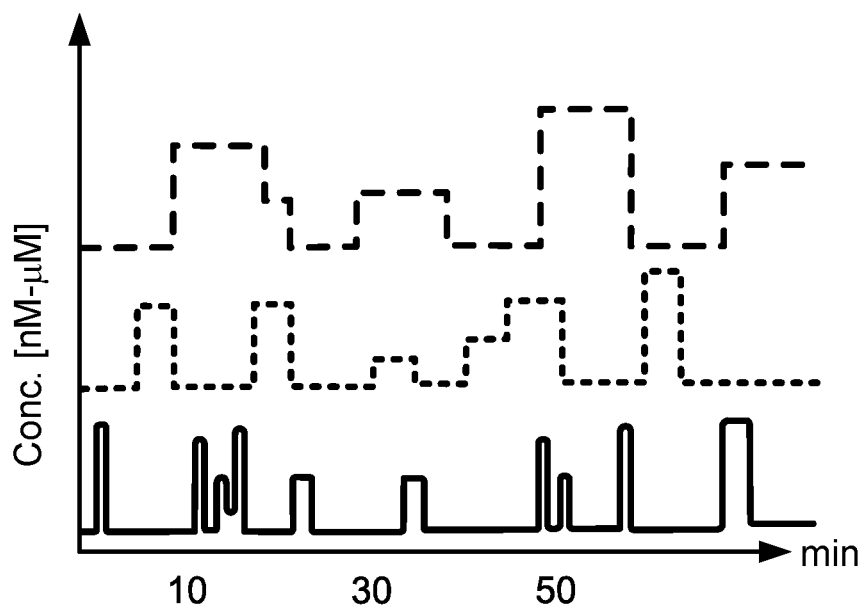
FIG. 5B illustrates schematically real-time monitoring intensities of the fluorescence signals produced by the three types of optical reporters as illustrated in FIG. 4, according to some embodiments.

FIG. 4 illustrates schematically three types of structure-switching reagents configured to bind to three different types of target molecules, target 1, target 2, and target 3, respectively, according to some embodiments. A respective type of optical reporters may be attached to each of the three types of structure-switching reagents. For example, a first type of optical reporters may be attached to the first type of structure-switching reagent for producing fluorescence signals in the green wavelengths upon binding to target 1; a second type of optical reports may be attached to the second type of structure-switching reagent for producing fluorescence signals in the yellow wavelengths upon binding to target 2; and a third type of optical reporters may be attached to the third type of structure-switching reagent for producing fluorescence signals in the red wavelengths upon binding to target 3, as illustrated in FIG. 5A. By monitoring the intensities of the fluorescence signals in each wavelength range as a function of time, the rising and falling of the concentrations of the three target molecules can be monitored in real time, as illustrated in FIG. 5B. The structure-switching reagents may be attached to the end facet of an optical waveguide as illustrated in FIG. 4, or may be attached to the sidewall of an optical waveguide as illustrated in FIG. 2. When the structure-switching reagents are attached to the end facet of an optical waveguide, the optical reporters attached to the structure-switching reagents may be excited by a direct optical field; whereas when the structure-switching reagents are attached to the sidewall of an optical waveguide, the optical reporters attached to the structure-switching reagents may be excited by an evanescent optical field.

Figure 6:
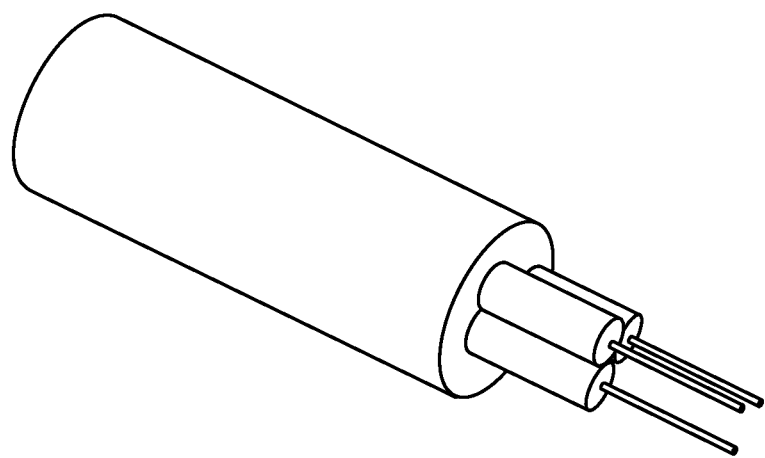
FIG. 6 illustrates schematically an optical probe that includes three optical fibers coupled to three different types of structure-switching reagents according to some embodiments.

FIG. 6 illustrates schematically an optical probe that includes three optical fibers coupled to three different types of structure-switching reagents (e.g., as those illustrated in FIG. 4).

Optical fibers are a type of optical waveguides. An optical fiber may include a high refractive index core surrounded by a cladding material with a lower refractive index. As such, light can be guided in the core by total internal reflection. Their optical readout signals have an enormous inherent bandwidth (intensity, wavelength, etc.), and have been leveraged in many sensing platforms [2-11]. Optical fibers may offer a multiplex advantage since different wavelengths can propagate simultaneously in either direction. Additionally, the compact geometry of optical fibers allows feedthroughs through, e.g., sealed chambers, skin, etc. One characteristic of an optical fiber is that it may support an evanescent wave. When total internal reflection takes place at an interface, the electric field strength of the incident light beam does not drop abruptly to zero at the interface; rather, it decreases exponentially from the interface into the surrounding lower refractive index medium over a distance of a few hundred nanometers (i.e., 200 nm). The electric field present in the surrounding medium can be absorbed by fluorophores near the interface and thus permits surface-specific fluorescence spectroscopy. This phenomenon has been extensively exploited in the development of surface-specific immunoassays exhibiting high sensitivity. See, e.g., Oroszlan, P., et al. *Sensors and Actuators B*, vol. 11, 1993, pp. 301-305 and Miyajima, Kumiko, et al. *Environmental Monitoring and Assessment*, vol. 182, 2011, pp. 233-241 The waveguide binding configuration described herein makes use of the evanescent wave propagating near the surface, and the surface binding of an analyte is detected by changes in fluorescence intensity as it enters or leaves the zone near the surface.

According to some embodiments, an optical probe may exploit one or more of the following: (1) a micron tip of an optical fiber for minimal invasiveness and high spatial resolution (i.e., can be inserted in specific locations); (2) the evanescent wave phenomenon to eliminate background autofluorescence from complex in vivo environments; (3) high sensitivity measurements; and (4) the multiplexing capability with the possibility of a multi-color bundle.

The optical fibers may be configured to have suitable characteristics for an optical probe. Single-mode and multimode fibers are commercially available and have low attenuation (e.g., ~3-5 dB/km at wavelengths of 650-850 nm, which is the bandwidth some dyes emit). The background fluorescence of the optical fiber is also a consideration in selecting a suitable optical fiber for the optical probe.

Figure 7A:
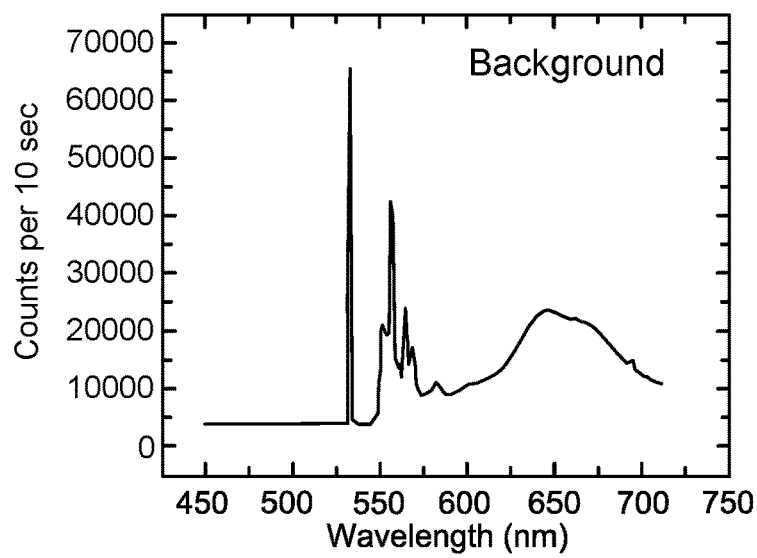
FIG. 7A shows an exemplary background emission spectrum of an optical fiber when excited with light according to some embodiments.
Figure 7B:
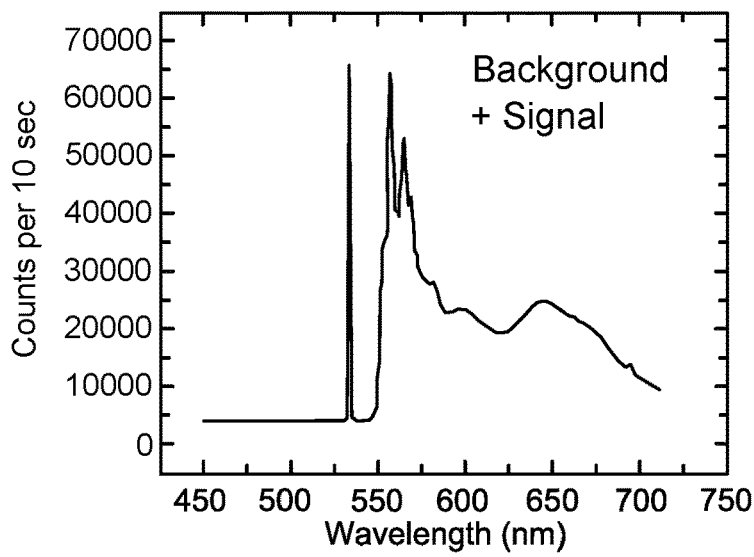
FIG. 7B shows an exemplary emission spectrum of an optical fiber that includes both background emission and fluorescence signals according to some embodiments.
Figure 7C:
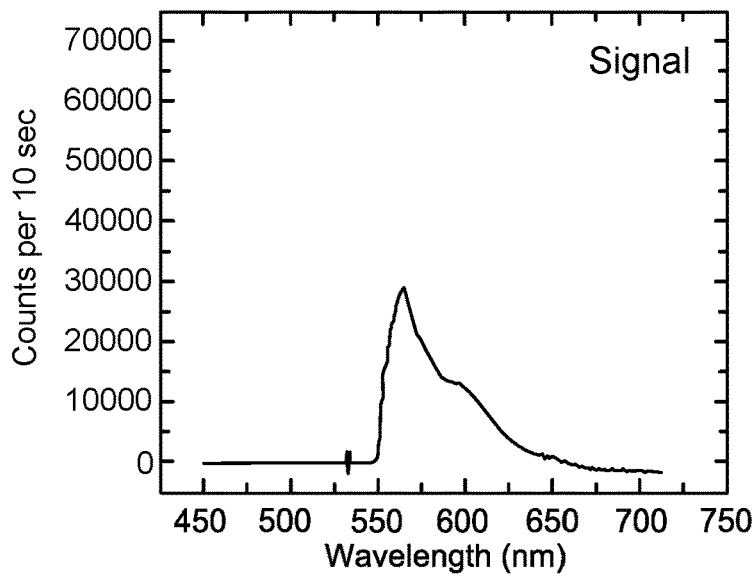
FIG. 7C shows an emission spectrum of the fluorescence signals obtained by subtracting the background spectrum shown in FIG. 7A from the emission spectrum shown in FIG. 7B according to some embodiments.

FIG. 7A shows an exemplary background emission spectrum of an optical fiber when excited with light at 405 nm, 530 nm, and 630 nm excitation wavelengths, using appropriate laser lines and bandpass and longpass filters in the excitation and detection paths. FIG. 7B shows an exemplary emission spectrum of an optical fiber that includes both background emission and fluorescence signals. FIG. 7C shows an emission spectrum of the fluorescence signals obtained by subtracting the background spectrum shown in FIG. 7A from the emission spectrum shown in FIG. 7B.

Background emissions likely originate from impurities in the optical fiber (color centers), and can overlap with the background. To minimize the fiber background, different types of fibers, including single-mode fibers and multimode fibers, multimode fibers with different core diameters (e.g., 100 μm, 62.5 μm, 50 μm), step-index and graded-index multimode fibers, and multimode fibers with high and low OH contents, are tested.

Figure 8:
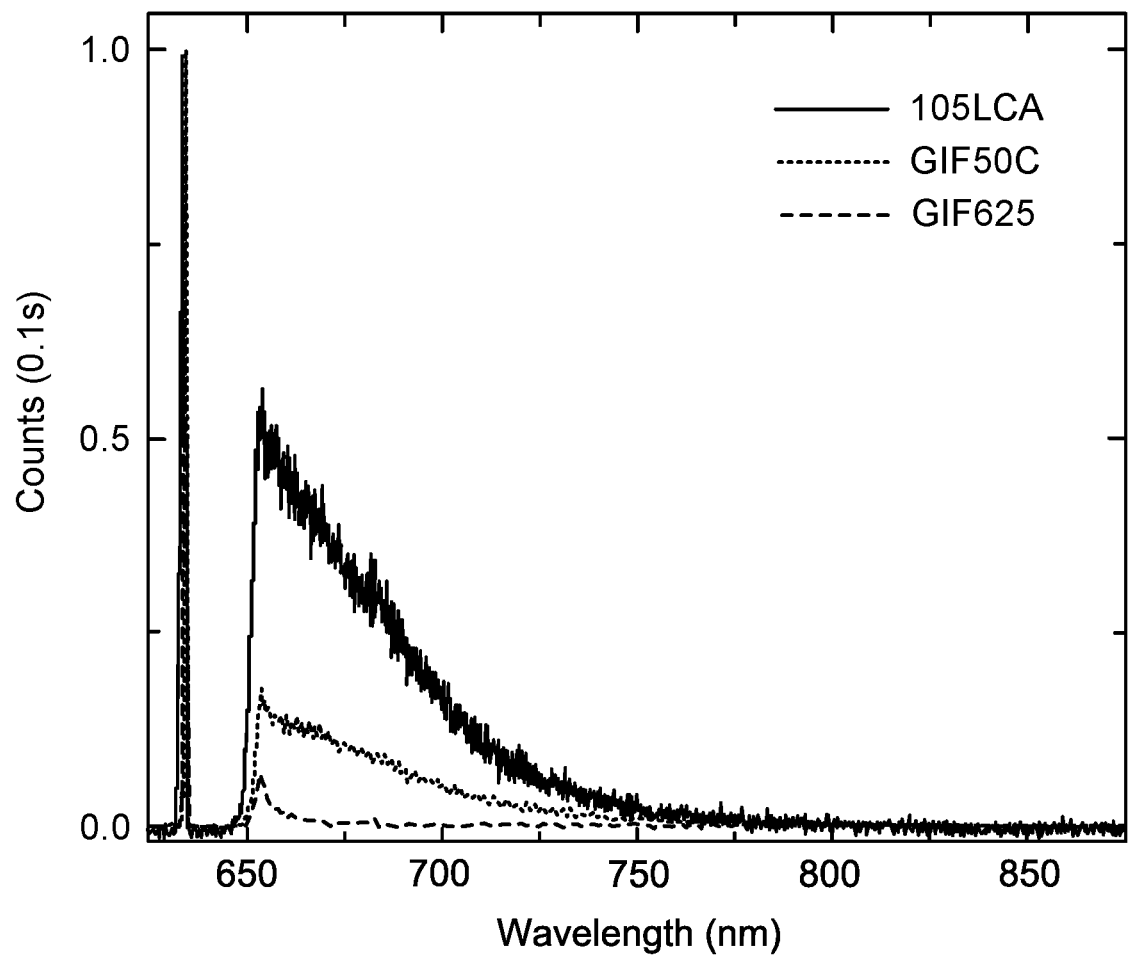
FIG. 8 shows exemplary background emission spectra from three different types of optical fibers.

FIG. 8 shows exemplary background emission spectra from three different types of optical fibers (e.g., FG105LCA; GIF50C and GIF625 Manufactured by Thorlabs). To minimize background counts from the environment, reinforced tubing is used instead of standard tubing for multimode fibers. As illustrated in FIG. 8, the background is least significant when using a graded-index multimode fiber (Thorlabs GIF625) with a core diameter of 62.5 μm and an operating wavelength longer than 650 nm. Since the residual background counts from the fiber are constant, they can be subtracted from the measurement (e.g., as illustrated in FIGS. 7A-7C).

In order to achieve a near-field sensing, different approaches for preparing the tip of an optical fiber can be used to promote evanescent field interaction with surface-bound aptamers and maximize sensing area. Exemplary approaches include but are not limited to HF etching and fiber tapering according to some embodiments.

In an HF etching approach, protective plastic covering of fibers, if any, is removed using a fiber stripping tool to expose only the tip (e.g., a few inches) of the fiber end. The fibers can be incubated in hydrofluoric acid (e.g., 49% hydrofluoric acid diluted in a 3:1 ratio with water) for various amounts of time. It was observed that the effectiveness of the cladding removal is optimal after 50 min incubation time. However, results may vary depending on tip configurations (hollow tip, narrow, or flat tips) in addition to deformations observed along the etched profile which varied from fiber to fiber.

Alternatively, the tip of the fiber can be tapered. For example in some embodiments, a heat-and-pull tapering can be performed on the tip. An exemplary protocol is described in, e.g., Lai, Yu-Hung et al. "Fiber taper characterization by optical backscattering reflectometry." *Optics Express*, vol. 25, 18 Sep. 2017, pp. 22312-22327. In some embodiments, the heat- and taper method can involve one or more of the following steps. Several inches of the plastic coating may be stripped from a central section of the fiber, and the ends may be attached to fiber holders mounted on translational stages. A ceramic micro-heater may be centered above the fiber and lowered to surround the fiber during the tapering process. While exposed to the heater, the fiber ends may be pulled, e.g., at a speed of 0.1 millimeters per second. The taper profile of the optical fiber tip may be adjusted by varying the temperature of the heater and the pulling length. Upon completion of pulling, the heater is removed from the fiber and the fiber is pulled (e.g., at 0.1 millimeters per second) until the fiber splits at the taper waist.

Other methods of modifying a waveguide tip for attachment of aptamers are described in, e.g., Wang et al., *Biosensors and Bioelectronics* 66:11-18 (2015) and Tang et al., *Anal. Chim. Acta* 933: 182-188 (2016).

Figure 9:
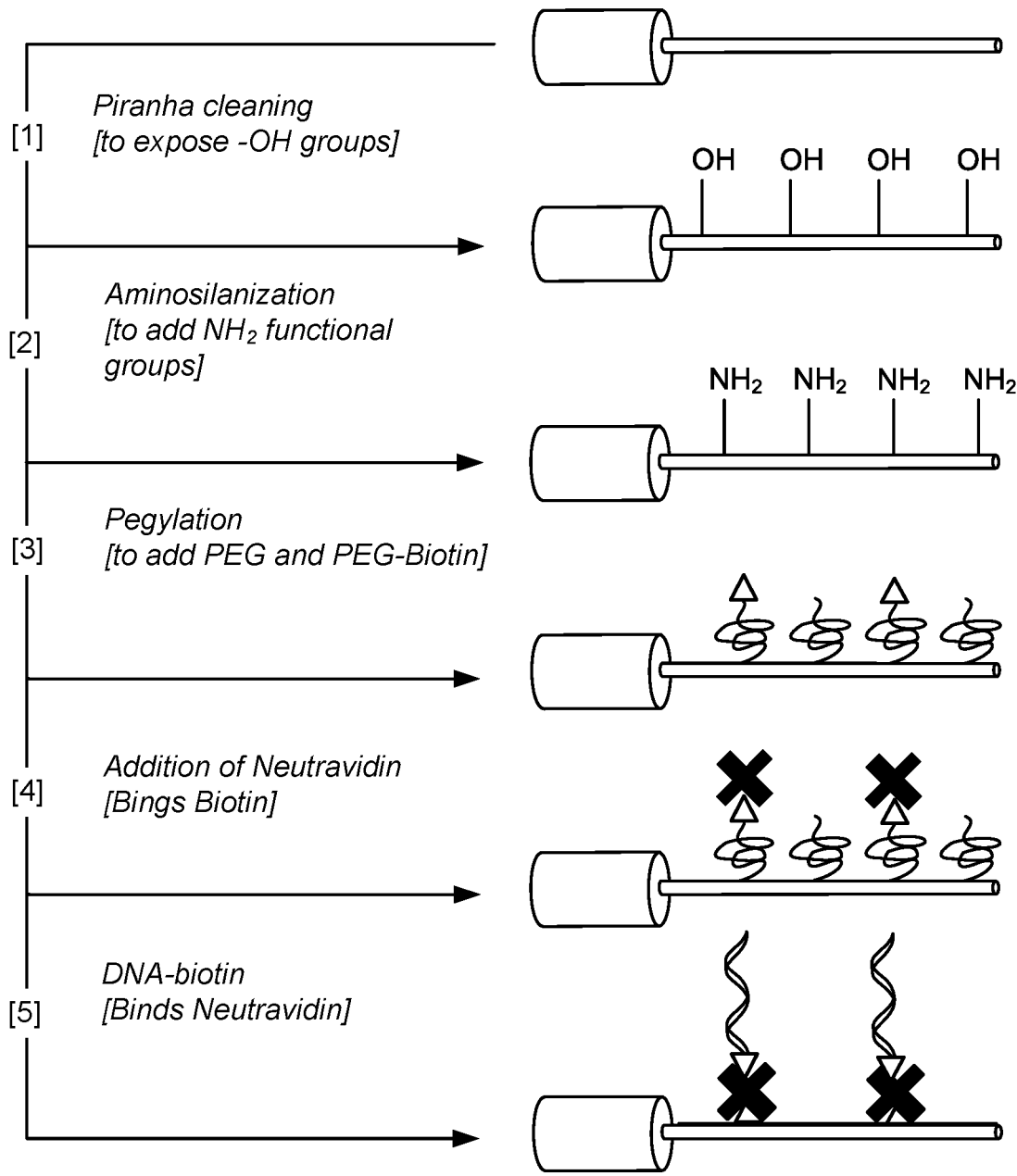
FIG. 9 illustrates exemplary steps of surface modification and passivation according to some embodiments.

Molecular switches can be attached to the waveguide core surface as desired. In some embodiments, to attach molecular switches (e.g., aptamers) to the fiber surface and to prevent non-specific binding of background serum proteins, surface modification and passivation processes can be used. In some embodiments, the molecular switch is linked directly to the core. In other embodiments, the molecular switch is linked via a linker. In some embodiments, the linkage to the core is via covalent linkages. In some embodiments, at least one non-covalent linkage is employed. For example, the molecular switch can be linked to the core via biotin-streptavidin interaction or via click chemistry. In some embodiments, biotinylated substrates are grafted onto a fiber or other waveguide through a reaction between surface-attached amino groups and N-hydroxysuccinimidyl ester groups at the end of biotin modified poly-ethylene glycol polymer chains (PEG) in anhydrous organic solutions. In some embodiments, a spacer molecule such as a PEG layer, is inserted to prevent non-specific binding and further enhance the specific interaction given its flexibility/mobility. In some embodiments, the PEG has a molecular weight of 300 g/mol-60,000 g/mol. In some embodiments, the PEG has on average between 20-200, e.g., 50-200, e.g., 80-120 units per molecule of PEG. After binding to the surface, the two binding sites left on streptavidin may be used to attach biotinylated aptamers or other biotinylated molecular switches. FIG. 9 illustrates exemplary steps of surface modification and passivation according to some embodiments. Where an evanescent field is used, the linker should be short enough so that the probe is maintained in the field. However, it can be advantageous for the linker to be of sufficient length to avoid fouling. For example, in some embodiments, the linker is longer than a 4 unit PEG molecule.

The density or number of molecular switches attached to the waveguide will affect sensitivity of the probe. In some embodiments, the tip of the waveguide has for example between $10^6$-$10^{12}$ (e.g., $10^7$-$10^{12}$, $10^7$-$10^{10}$, $10^8$-$10^9$) separate molecular switches. The surface density of the probes is optimized to achieve maximum signal amplitude and fast kinetics. If the density if too low, then the signal amplitude will be low. If the density is too high, then it can impede the kinetics of target binding. In some embodiments, kinetics is slowed down when the surface density exceeds $4 \times 10^{11}/cm^2$ (An Electrostatic Model for DNA Surface Hybridization, N. A. Melosh, Biophys. J. 2010). In some embodiments, the surface density used is 1-10×$10^9$, e.g., 2.5×$10^9$ molecules/$cm^2$.

The binding of fluorescently labeled-streptavidin and -DNA to the surface may be observed and characterized using fluorescence microscopy. Multiple fluorophore pairs (i.e. photophysical properties/FRET efficiency), such as Alexa/Cye/ATTO fluorophores, along with dynamic and static quenchers like Dab/BHQ dark quenchers, are tested. In some embodiments, surface density may be optimized by changing the PEG:PEG-Biotin ratio and checking for the optimal coverage of molecular switches on the surface to ensure probe availability, fast binding kinetics, and maximum signal detection with minimal background noise (optimal ratio=1:50).

II. OPTICAL BIOSENSOR SYSTEM

Figure 10:
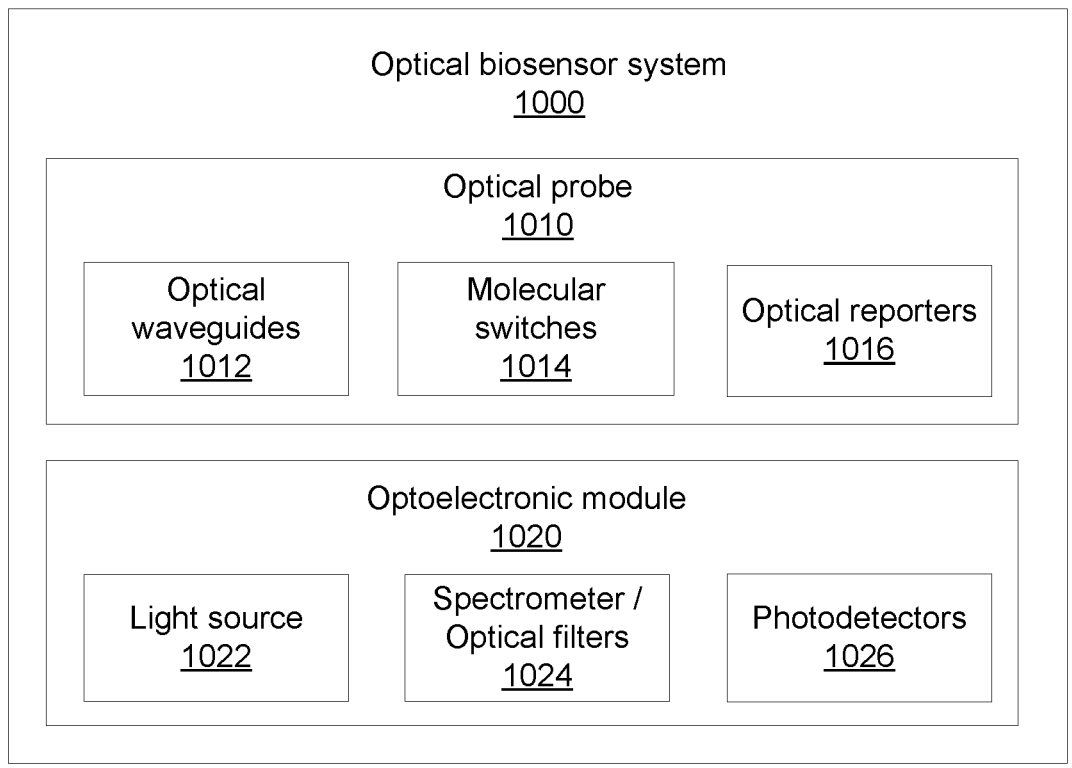
FIG. 10 is a schematic block diagram of an optical biosensor system according to some embodiments.

FIG. 10 is a schematic block diagram of an optical probe system 1000 according to some embodiments. The optical probe system 1000 includes an optical probe 1010. The optical probe 1010 may include one or more optical waveguides 1012 (e.g., optical fibers), molecular switches 1014 (e.g., conformation-changing aptamers) attached to the tips of the optical waveguides 1012, and optical reporters 1016 (e.g., fluorescence labels) attached to the molecular switches 1014, as discussed above.

The optical probe system 1000 further includes an optoelectronic module 1020. The optoelectronic module 1020 includes a light source 1022 configured to emit light to be coupled into the optical waveguides 1012 of the optical probe 1010. For example, the light source 1022 may include one or more light emitting diodes (LEDs) or laser sources configured to emit light in one or more wavelength ranges (e.g., in green, yellow, and red wavelength ranges). The light emitted by each LED or laser source may be coupled into a respective waveguide, and to be propagated to a tip of the respective waveguide for generating an optical field at the tip and/or an evanescent optical field at a sidewall of the tip. The evanescent optical field may extend about few tens of nanometers to about a few hundreds of nanometers (e.g., 200 nm) from the sidewall into the surrounding medium. The optical field (or the evanescent optical field) may excite the optical reporters 1016 attached to the molecular switches 1014. The optical reporters 1016 may emit fluorescence light or produce a change in fluorescent light when the molecular switches 1014 bind to target molecules. The fluorescence light may be at wavelengths that are longer than the wavelengths of the excitation light. The fluorescent light emitted by the molecular switches is transmitted through the waveguide to a detector, which can quantify changes in signal from the waveguide. Accordingly, the system does not require any addition of reagents to a sample for detection of the target in the sample. The system can excite the molecular switch and receive signal via the waveguide from the molecular switch indicating target concentration without administration of free aptamers, nucleic acids, or other probes to the sample (e.g., animal). Moreover, the system is capable of continuous monitoring of target molecule concentration in the sample. As noted previously, the sample can be a live animal (e.g., a human).

The optoelectronic module 1020 further includes a spectrometer or optical filters 1024 configured to filter the fluorescence light emitted by the optical reporters 1016. The optoelectronic module 1020 further includes one or more photodetectors 1026 configured measure the intensities of the fluorescence light.

Figure 11:
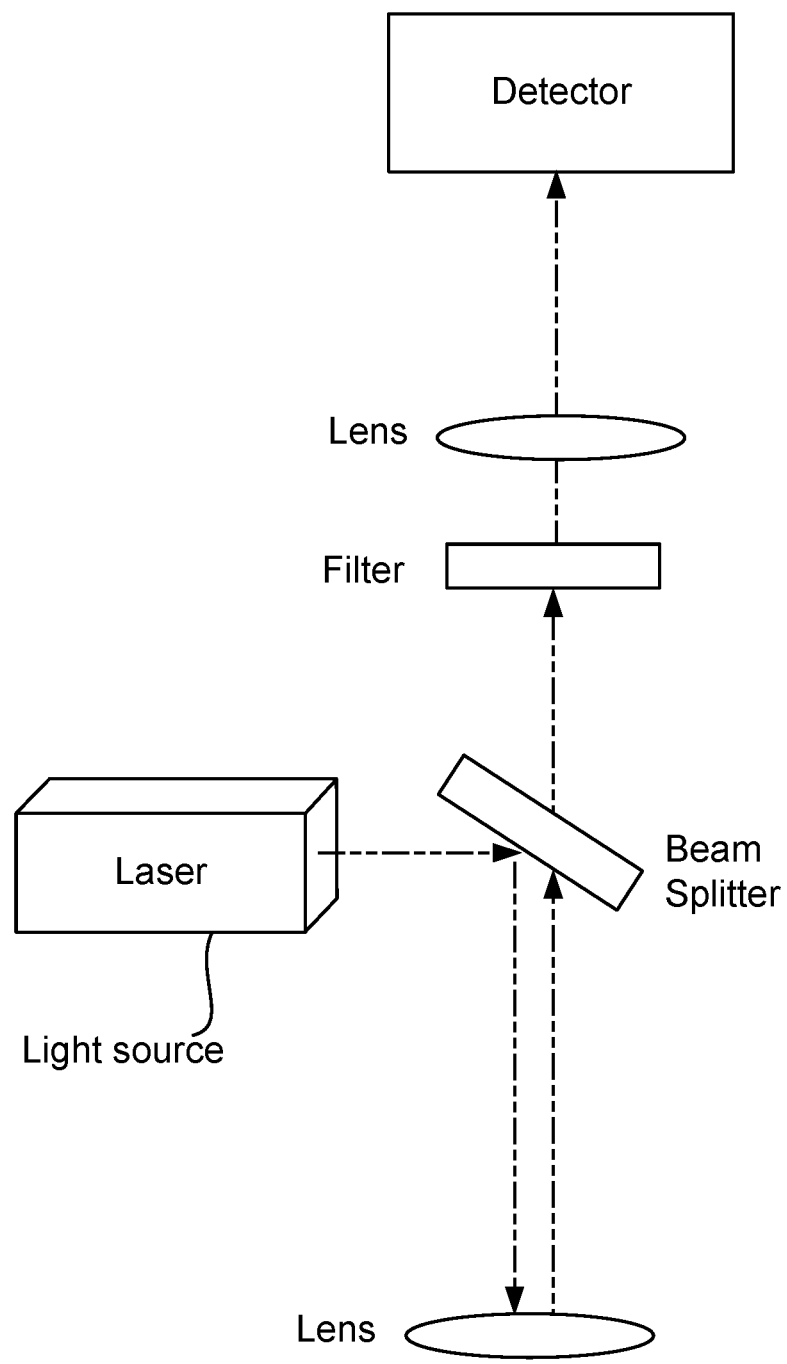
FIG. 11 shows a schematically diagram of an optoelectronic module that may be used in conjunction with an optical probe in an optical biosensor system according to some embodiments.

FIG. 11 shows a schematically diagram of an optoelectronic module that may be used in conjunction with an optical probe in an optical biosensor system according to some embodiments. The optoelectronic module includes a light source (e.g., a laser source) configured to emit excitation light in certain wavelength range to excite optical reporters on the molecular switches. The optoelectronic module may include an optical beam splitter configured to reflect the excitation light emitted by the light source toward a first collimating lens.

The collimated excitation light may be coupled into a waveguide of an optical probe, and may excite fluorescence labels attached to the molecular switches of the optical probe, which may emit fluorescence light in response to the molecular switches binding to target molecules, as discussed above. The fluorescence light may be in a wavelength range that is longer than the wavelength range of the excitation light. As an example, the excitation light may be in the green wavelength range, and the fluorescence light may be in the yellow wavelength range. The fluorescence light may be coupled back into the waveguide of the optical probe and be detected by the optoelectronic module as illustrated in FIG. 11.

The optical beam splitter may be configured to transmit the fluorescence light. For example, the optical beam splitter may be a dichroic beam splitter configured to have high reflectance values in the wavelength range of the excitation light and high transmittance values in the wavelength range of the fluorescence light. In some other embodiments, the optical beam splitter may be a polarization beam splitter, and the light source may be configured to produce polarized light. In some embodiments, the power of the excitation light emitted by the light source is low in order to reduce photobleaching. In some embodiments, a power of the excitation light emitted by the light source ranges from about 1 nW to about 300 nW, or from about 10 nW to about 200 nW, or from about 40 nW to about 150 nW, or from about 50 nW to about 100 nW (e.g., about 1 nW to about 280 nW, about 1 nW to about 260 nW, about 1 nW to about 240 nW, about 1 nW to about 220 nW, about 1 nW to about 200 nW, about 1 nW to about 180 nW, about 1 nW to about 160 nW, about 1 nW to about 140 nW, about 1 nW to about 120 nW, about 1 nW to about 100 nW, about 1 nW to about 80 nW, about 1 nW to about 60 nW, about 1 nW to about 40 nW, about 1 nW to about 20 nW, or about 1 nW to about 10 nW; e.g., about 1 nW, 5 nW, 10 nW, 20 nW, 30 nW, 40 nW, 50 nW, 60 nW, 70 nW, 80 nW, 90 nW, 100 nW, 110 nW, 120 nW, 130 nW, 140 nW, 150 nW, 160 nW, 170 nW, 180 nW, 190 nW, 200 nW, 210 nW, 220 nW, 230 nW, 240 nW, 250 nW, 260 nW, 270 nW, 280 nW, 290 nW, or 300 nW). In certain embodiments, a power of the excitation light emitted by the light source ranges from about 300 nW to about 3 µW, or from 500 nW to about 2.5 µW, or from 1 µW to about 2 µW, or from 1.5 µW to about 2 µW (e.g., about 500 nW to about 3 µW, about 700 nW to about 3 µW, about 900 nW to about 3 µW, about 1 µW to about 3 µW, about 1.2 µW to about 3 µW, about 1.4 µW to about 3 µW, about 1.6 µW to about 3 µW, about 1.8 µW to about 3 µW, about 2 µW to about 3 µW, about 2.2 µW to about 3 µW, about 2.4 µW to about 3 µW, about 2.6 µW to about 3 µW, about 2.8 µW to about 3 µW, about 300 nW to about 2.8 µW, about 300 nW to about 2.6 µW, about 300 nW to about 2.4 µW, about 300 nW to about 2.2 µW, about 300 nW to about 2 µW, about 300 nW to about 1.8 µW, about 300 nW to about 1.6 µW, about 300 nW to about 1.4 µW, about 300 nW to about 1.2 µW, about 300 nW to about 1 µW, about 300 nW to about 800 nW, or about 300 nW to about 600 nW).

In some embodiments, for unprecedented detection sensitivity, the whole setup may be isolated from any background light sources through elements such as reinforced tubing of fibers, compact building procedures and shielding. Reducing the background signal may increase the signal-to-noise ratio and allow for detecting smaller changes in the emission signal. A detector with minimal dark counts (noise), such as a SPCM, may be used for the same reasons.

An optical sensor system described herein can have multiple optical probes, such as at least a first optical probe and a second optical probe. This allows for multiplexing, i.e., detecting two structurally-different targets. As discussed elsewhere herein, each optical probe in the optical sensor system can have an optical waveguide having a first end and a second end. The first end of the optical probe can be configured to receive excitation light to be propagated through the optical waveguide and to be emitted from the second end into a surrounding medium or alternatively emitted from a tapered section in the middle of the waveguide and into the medium surrounding the tapered section. Further, the second end or a tapered middle region of the optical waveguide in the optical probe can have one or more molecular switches attached to a facet or a sidewall of the second end or the middle region of the optical waveguide, in which the molecular switches are configured to change conformation upon binding to a corresponding target molecule. Moreover, each molecular switch can have one or more optical reporters attached. The optical reporters, when exposed to the excitation light, can produce an optical signal change upon binding of the respective molecular switch to the corresponding target molecule in the surrounding medium. The optical signal produced by the optical reporter (e.g., from molecular switches at the second end) can be coupled back into the optical waveguide via the second end and propagated through the optical waveguide to be emitted from the first end. Alternatively, in embodiments in which the molecular switches are at the tapered middle region, the optical signal can be propagated to the second end.

In some embodiments of the optical probe, the molecular switches can be attached to a sidewall of the second end of the optical waveguide. The optical reporters attached to each molecular switch can produce an optical signal when exposed to the excitation light. Further, when the molecular switches are at the second end of the optical waveguide, the optical signal produced can be propagated through the optical waveguide and emitted from the first end of the optical waveguide. In these embodiments, when the molecular switches are located at the second end of the optical waveguide, the molecular switches can be inserted into the surrounding medium for target molecule binding, without changing the shape of the optical waveguide.

In some other of the optical probe, the molecular switches can be attached to a sidewall of the middle region of the optical waveguide. The optical reporters attached to each molecular switch can produce an optical signal when exposed to the excitation light. In some embodiments, the middle region of the optical probe can be a tapered middle region. In these embodiments, an end of the optical probe can be configured to receive excitation light to be propagated through the optical probe and to be emitted from the tapered middle region of the optical probe and into the medium surrounding the tapered middle region. Further, when the molecular switches are at the middle region (e.g., a tapered middle region) of the optical waveguide, the optical signal produced can be propagated through the optical waveguide and emitted from the second end of the optical waveguide. In these embodiments, the optical waveguide can form a U-shaped or V-shaped optical waveguide in order to insert the molecular switches, which are located in the middle region of the optical waveguide, into the surrounding medium for target molecule binding.

In some multiplexing embodiments, each optical probe in an optical sensor system can have molecular switches attached to a facet or a sidewall of the second end or the middle region of the optical waveguide, where the molecular switches in each optical probe bind to a different target molecule. For example, an optical sensor system with two optical probes can have a first molecular switch on a first optical probe that binds to a first target molecule and a second molecular switch in a second optical probe that binds to a second target molecule that is structurally-different from the first target molecule. When exposed to excitation light, different optical signals can be produced upon binding of the respective molecular switch to its corresponding target molecule in the surrounding medium.

In other embodiments, ratiometric measurements from each molecular switch can be obtained. For example, ratiometric measurements can be used to more accurately measure the concentration of a target molecule or the concentrations of two different target molecules. In these embodiments, the molecular switches can be attached to optical reporters that contain a donor fluorophore and an acceptor fluorophore. The donor fluorophore and the acceptor fluorophore can be in proximity of each other to produce a FRET signal depending on the interaction of the molecular switch and the target molecule. In some embodiments, when the molecular switch is bound to the target molecule, the donor fluorophore and the acceptor are in proximity of each other to produce a FRET signal. In other embodiments, when the molecular switch is not bound to the target molecule, the donor fluorophore and the acceptor are in proximity of each other to produce a FRET signal.

In ratiometric measurements, a ratio of the optical signal at the emission wavelength of the donor fluorophore and the optical signal at the emission wavelength of the acceptor fluorophore can be detected. In some embodiments, the optical signal from the donor fluorophore is higher than the optical signal from the acceptor fluorophore. In other embodiments, the optical signal from the donor fluorophore is lower than the optical signal from the acceptor fluorophore. In some embodiments, the FRET signal is generated when the acceptor and donor are brought into proximity due to binding of the molecular switch to the target. In these embodiments, when the target is bound the acceptor fluorophore signal can be higher than the donor signal. In other embodiments, the FRET signal is generated when the acceptor and donor are farther apart when the molecular switch binds to the target compared to when the molecular switch is unbound. In these embodiments, when the target is bound the donor fluorophore signal can be higher than the acceptor signal.

The optical probes and optical biosensor systems described herein can be used in various settings and in different applications in clinical and non-clinical environments. In one example, the optical probes and optical biosensor systems described herein can be used in acute clinical settings to monitor biomarkers (i.e., the biomarkers are bound by the molecular switches described herein) that are indicative of, e.g., heart attack (e.g., troponins), sepsis (e.g., lactates, cytokines, chemokines), stroke (e.g., adiponectins, fibrinogens, TNF-α), and immunological diseases (e.g., IgA, human serum albumin). In another example, the optical probes and optical biosensor systems described herein can be used to monitor biomarkers in chronic conditions, e.g., glucose and/or insulin levels in type-1 or type-2 diabetes, serotonin or other neuromodulators in neurological conditions. In yet another example, the optical probes and optical biosensor systems described herein can also be used to identify target binding in drug development.

III. METHOD OF MOLECULAR DETECTION

Figure 12:
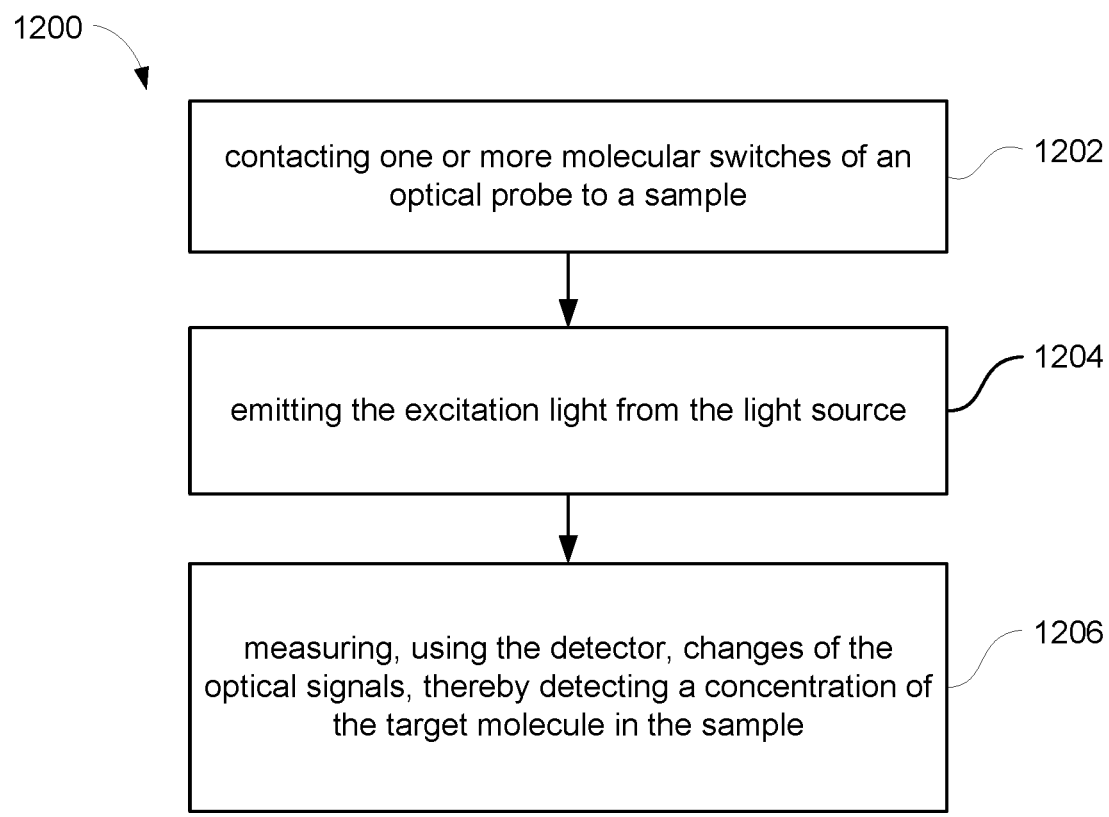
FIG. 12 is a flowchart illustrating a method of detection of a target molecule in a sample according to some embodiments.

FIG. 12 is a flowchart illustrating a method 1200 of detection of a target molecule in a sample according to some embodiments. The method 1200 may use an optical probe that includes one or more molecular switches attached to a tip of an optical waveguide and one or more optical reporters attached to the one or more molecular switches, as described above. The method 1200 may include, at 1202, contacting the one or more molecular switches of the optical probe to the sample. The method 1200 further includes, at 1204, emitting the excitation light from the light source. For example, light emitted by a light source may be coupled into the optical waveguide to be propagated to a tip of the optical waveguide to which the one or more molecular switches are attached. The method 1200 further includes, at 1206, measuring, using the detector, changes of the optical signals. Thus, a concentration of the target molecule in the sample may be measured.

In some embodiments, the system can be isolated from background light sources. For example, elements such as reinforced tubing of fibers, compact building procedures and shielding can be applied to reduce external light contamination into the system. Reducing the background signal increases the signal-to-noise ratio and allows for detection of smaller changes in the emission signal. Moreover, one can use a detector with minimal dark counts (noise) such as a single photon counting module (SPCM).

In some embodiments, the detection of a target molecule using an optical probe or an optical sensor system described herein can be ratiometric. For example, the molecular switches can be attached to optical reporters that contain a donor fluorophore and an accepter fluorophore. In some embodiments, when the molecular switches are bound to a target molecule, the donor fluorophore and the acceptor fluorophore are in proximity of each other to produce a FRET signal. In other embodiments, when the molecular switches are not bound to a target molecule the donor fluorophore and the acceptor fluorophore are in proximity of each other to produce a FRET signal. Ratiometric measurements can also be used when detecting two different target molecules, in which a FRET signal is produced when either the first target molecule or the second target molecule is bound to the molecular switches. A ratio of the optical signal at the emission wavelength of the donor fluorophore and the optical signal at the emission wavelength of the acceptor fluorophore can be taken.

In another example, when the optical sensor system contains multiple optical probes, where each optical probe contains molecular switches, the molecular switches in different optical probes can bind to different target molecules. The molecular switches in a first optical probe can be configured to generate a first optical signal at a first wavelength when the molecular switches bind to a first target molecule, and the molecular switches in a second optical probe can be configured to generate a second optical signal at a second wavelength when the molecular switches bind to a second target molecule.

The measuring can include measuring the first optical signal at the first wavelength and the second optical signal at the second wavelength to generate a first value representing the first optical signal and a second value representing the second optical signal. In some embodiments, the first wavelength and the second wavelength are far apart from each other. For example, the first wavelength can be in the green wavelength range (e.g., between 500 nm and 570 nm, 500 nm and 560 nm, 500 nm and 550 nm, 500 nm and 540 nm, 500 nm and 530 nm, 500 nm and 520 nm, 500 nm and 510 nm, 510 nm and 570 nm, 520 nm and 570 nm, 530 nm and 570 nm, 540 nm and 570 nm, 550 nm and 570 nm, or 560 nm and 570 nm) and the second wavelength can be in the red wavelength range (e.g., between 620 nm and 750 nm, 620 nm and 740 nm, 620 nm and 730 nm, 620 nm and 720 nm, 620 nm and 710 nm, 620 nm and 700 nm, 620 nm and 690 nm, 620 nm and 680 nm, 620 nm and 670 nm, 620 nm and 660 nm, 620 nm and 650 nm, 620 nm and 640 nm, 620 nm and 630 nm, 630 nm and 750 nm, 640 nm and 750 nm, 650 nm and 750 nm, 660 nm and 750 nm, 670 nm and 750 nm, 680 nm and 750 nm, 690 nm and 750 nm, 700 nm and 750 nm, 710 nm and 750 nm, 720 nm and 750 nm, 730 nm and 750 nm, or 740 nm and 750 nm). In other examples, the first wavelength can be below 500 nm (e.g., between 420 nm and 500 nm, between 440 nm and 500 nm, between 460 nm and 500 nm, or between 480 nm and 500 nm) and the second wavelength can be above 750 nm (e.g., between 750 nm and 2400 nm, between 750 nm and 2300 nm, between 750 nm and 2200 nm, between 750 nm and 2100 nm, between 750 nm and 2000 nm, between 750 nm and 1900 nm, between 750 nm and 1800 nm, between 750 nm and 1700 nm, between 750 nm and 1600 nm, between 750 nm and 1500 nm, between 750 nm and 1400 nm, between 750 nm and 1300 nm, between 750 nm and 1200 nm, between 750 nm and 1100 nm, between 750 nm and 1000 nm, between 750 nm and 900 nm, between 750 nm and 800 nm, between 750 nm and 2500 nm, between 800 nm and 2500 nm, between 850 nm and 2500 nm, between 900 nm and 2500 nm, between 950 nm and 2500 nm, between 1000 nm and 2500 nm, between 1500 nm and 2500 nm, or between 2000 nm and 2500 nm).

Figure 13:
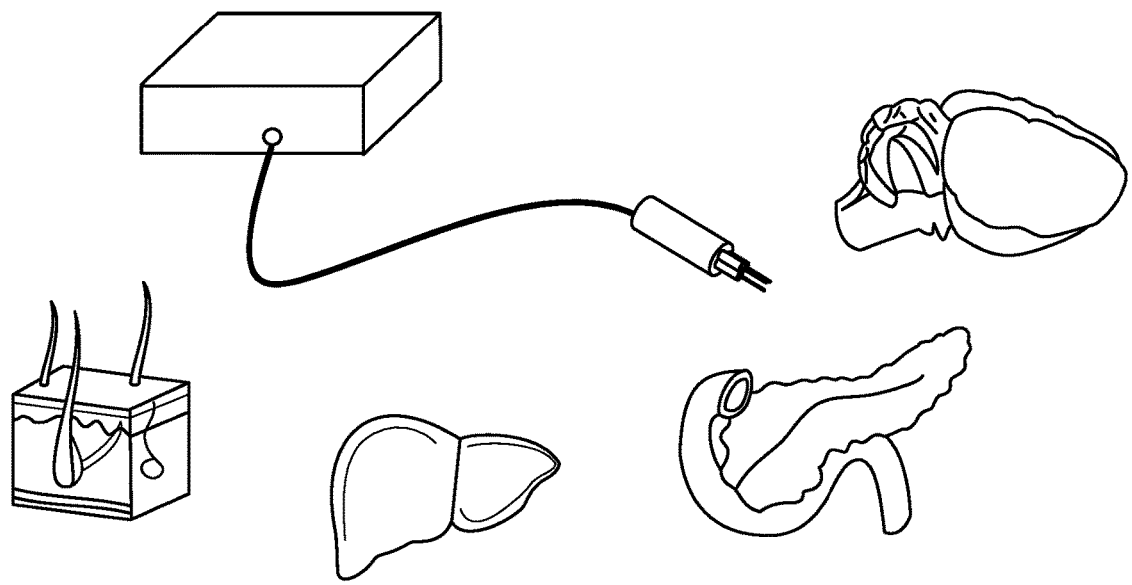
FIG. 13 illustrates schematically that an optical probe may be used for real-time in vivo monitoring of molecules.

FIG. 13 illustrates schematically that an optical probe may be used for real-time in vivo monitoring of molecules. In some embodiments, the method of detecting a target molecule can be used in an in vivo sample (e.g., an in vivo tissue) of a living subject (e.g., an animal or a human), where the measuring of changes of the optical signals to detect the concentration of the target molecule in the sample can be performed continuously. Optical biosensor systems may have a variety of applications. Exemplary applications include but are not limited to the following.

Biomedical research. Optical biosensor systems can be used as general tools for measuring proteins, small molecules, and other biomolecules in biomedical research, including neuroscience, immunology, infectious diseases, cancer, and others.

Diabetes management. Optical probes establish a new route for glucose sensing with a robust, calibration free and long-lasting glucose-meter. In some embodiments, one can integrate glucose, insulin and glucagon detection in a single sensor (for example, different molecular switches that bind to glucose, insulin and glucagon can be attached to separate waveguides).

Monitoring of therapeutic agents. Optical probes can be used to continuously monitor drugs and body's reaction to the drugs (pharmacokinetics and pharmacodynamics).

Monitoring of target molecules naturally released in the sample.

Continuous monitoring of health state (e.g., cytokines, hormones, etc.).

Continuous monitoring of human performance.

Real-time/end-point optical sensors/in vivo/in vitro sensing.

Change aptamers/light activatable aptamers

Incorporate a resonator or cavity for signal enhancement (possibility of attaching photonic structures to fibers).

Measure lifetime/anisotropy instead of intensity (circumvent photobleaching problems).

IV. EXAMPLES

A. Exemplary Real-Time Biosensor Systems

The optical biosensor system may be used in a variety of measurement applications, where the fiber can be inserted into biological samples (e.g., blood or cerebrospinal fluid). The optical biosensor system may also be used in in vivo applications, where the fiber can be placed inside a syringe that can be inserted under the skin.

Figure 14:
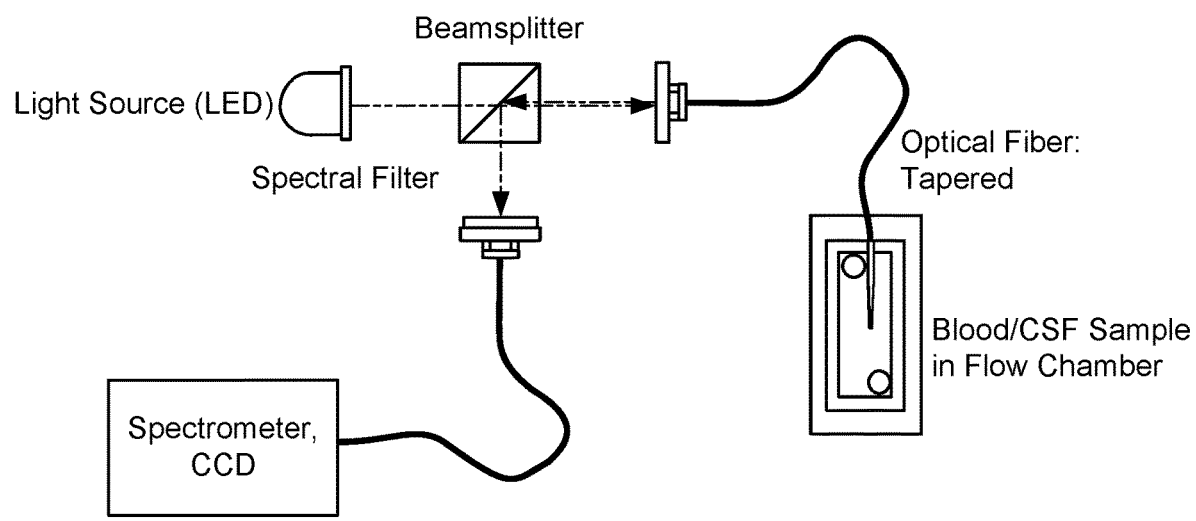
FIG. 14 illustrates schematically an optical biosensor system using a beamsplitter and free space paths to couple to and from a (optionally tapered) fiber in a flow chamber, according to some embodiments.

FIG. 14 illustrates schematically an optical biosensor system using a beamsplitter and free space paths to couple to and from a tapered fiber in a flow chamber, according to some embodiments. Spectral filtering and detection may be performed using a spectrometer and a charge-coupled device (CCD).

Figure 15:
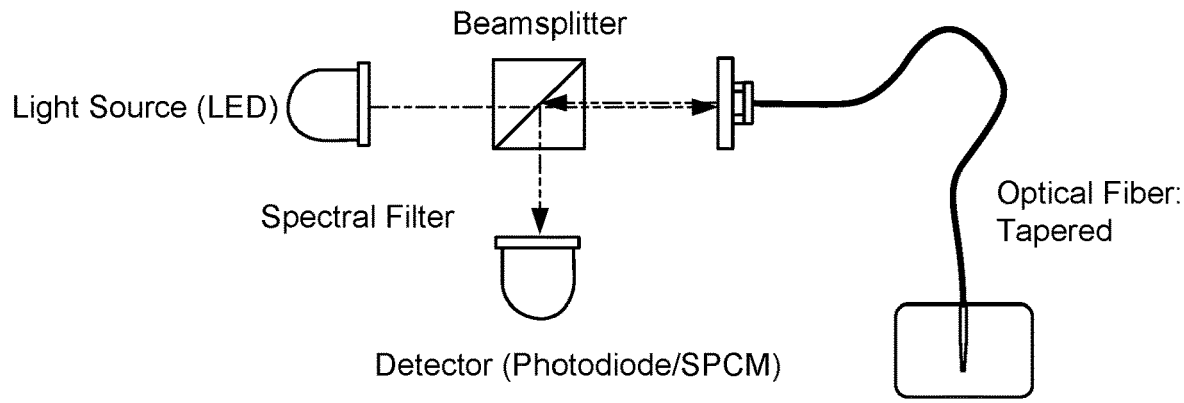
FIG. 15 illustrates schematically an optical biosensor system using a beamsplitter and free space paths to couple to and from a tapered fiber, which is placed in a syringe that can be inserted into living tissues (e.g., human tissues), according to some embodiments.

FIG. 15 illustrates schematically an optical biosensor system using a beamsplitter and free space paths to couple to and from a tapered fiber, which is placed in a syringe that can be inserted into living tissues (e.g., human tissues), according to some embodiments. Spectral filtering may be performed using optical filters. Measurement may be performed using a photodiode or a single photon counting module (SPCM).

Figure 16:
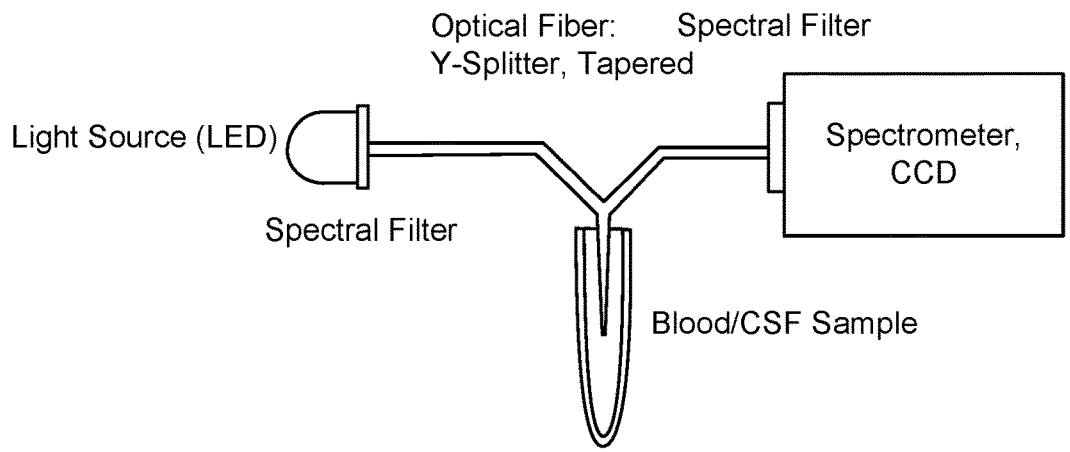
FIG. 16 illustrates schematically an optical biosensor system with a fully fiber-coupled setup using a Y-splitter according to some embodiments.

FIG. 16 illustrates schematically an optical biosensor system with a fully fiber-coupled setup using a Y-splitter according to some embodiments. Spectral filtering and detection are performed using a spectrometer and a CCD. The tapered fiber can be inserted into, for example, blood or cerebrospinal fluid (CSF) samples.

Figure 17:
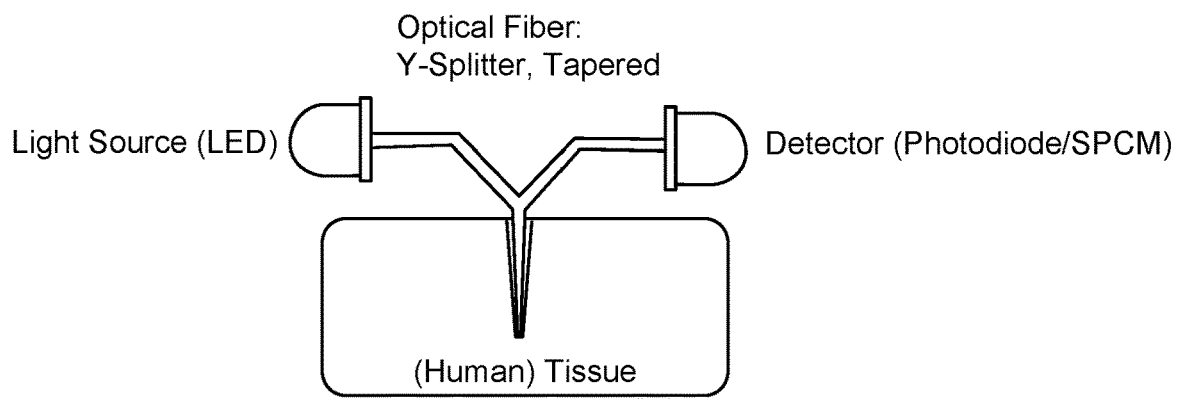
FIG. 17 illustrates schematically an optical biosensor system with a fully fiber-coupled setup using a Y-splitter, using optical filters for spectral filtering, according to some embodiments.

FIG. 17 illustrates schematically an optical biosensor system with a fully fiber-coupled setup using a Y-splitter, using optical filters for spectral filtering, according to some embodiments. The tapered fiber can be inserted into a syringe, which can be inserted into tissues (e.g., human tissue).

Figure 18:
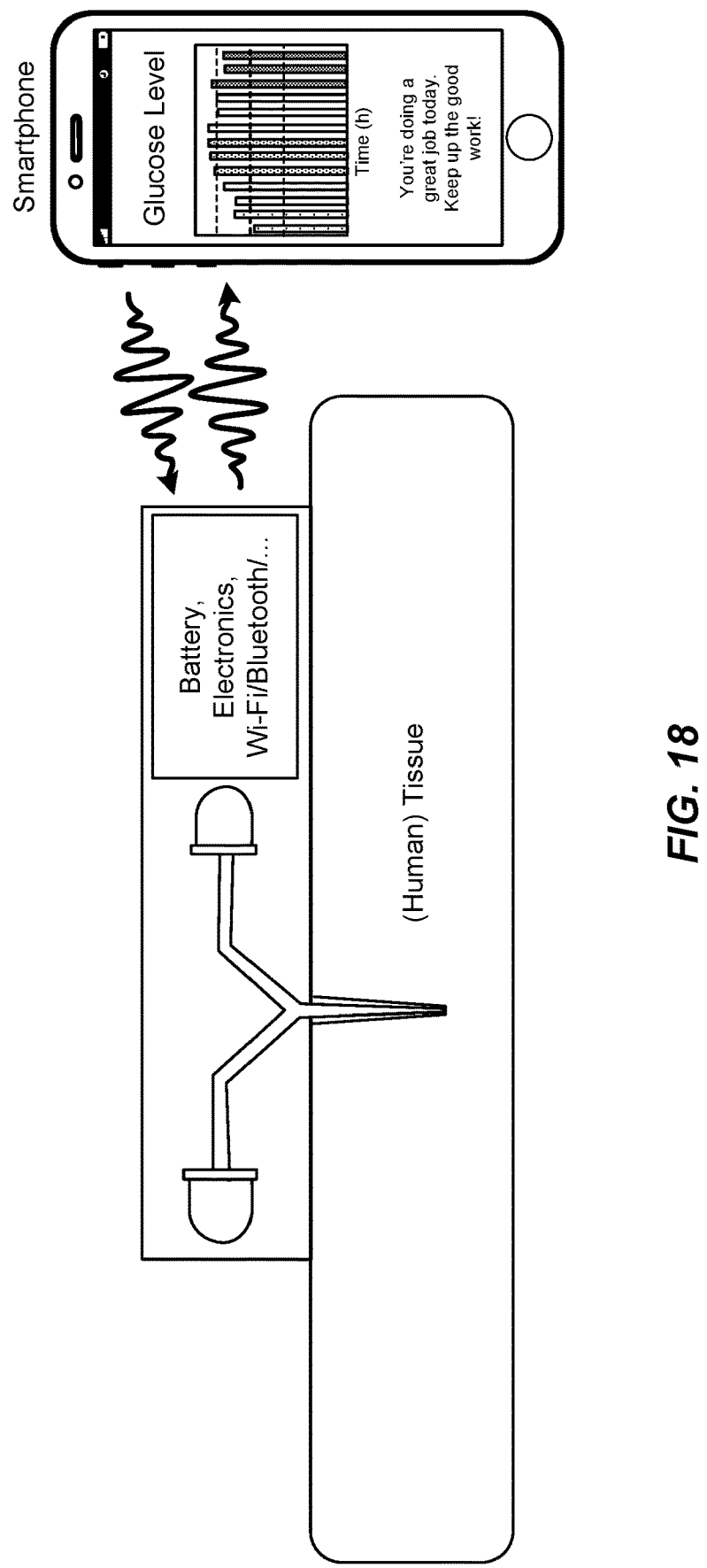
FIG. 18 illustrates schematically a miniaturized optical biosensor system according to some embodiments. While detection of glucose is shown, it should be noted that any target molecules can be detected.

FIG. 18 illustrates schematically a miniaturized optical biosensor system, with an optical fiber inserted inside a syringe, which can be inserted into tissue and probe the analyte. Real-time data may be sent wirelessly to a mobile device, such as a smartphone.

According to some embodiments, in the various optical biosensor systems illustrated in FIGS. 14-18, the optical fiber may be connected to a real-time optoelectronic system. The optoelectronic system may excite the dyes on the aptamer optically, and use spectral filtering (spectrometer or optical filters) to separate emission from the biosensor from the excitation light. The optoelectronic system uses a detector (e.g., CCD, SPCM, APD, photodiode, etc.) to measure the fluorescence intensity (i.e., total count rate), time resolved changes in the count rates, or changes in the lifetime of the dye. By correlating the optical signal from the measured data to analyte concentration, precise and ultrafast real-time measurements of the target molecule concentration can be achieved. Real-time concentration changes of multiple analytes can be measured and sent to devices like smartphones through a wireless connection. Furthermore, the system can be readily multiplexed using a small fiber bundle (e.g., as illustrated in FIG. 6). This allows for a variety of applications including real-time adjustment of medication or early warning systems.

B. Real-Time Aptamer Switches: Engineering Principle

In order to achieve "real-time" measurements, one can convert the non-natural aptamer into an "aptamer-switch" that changes its molecular conformation upon binding and generates a change in the fluorescence signal. To this end, methods are developed to convert a non-natural aptamer into an aptamer-switch using an intra-molecular competition strategy.

Figure 19:
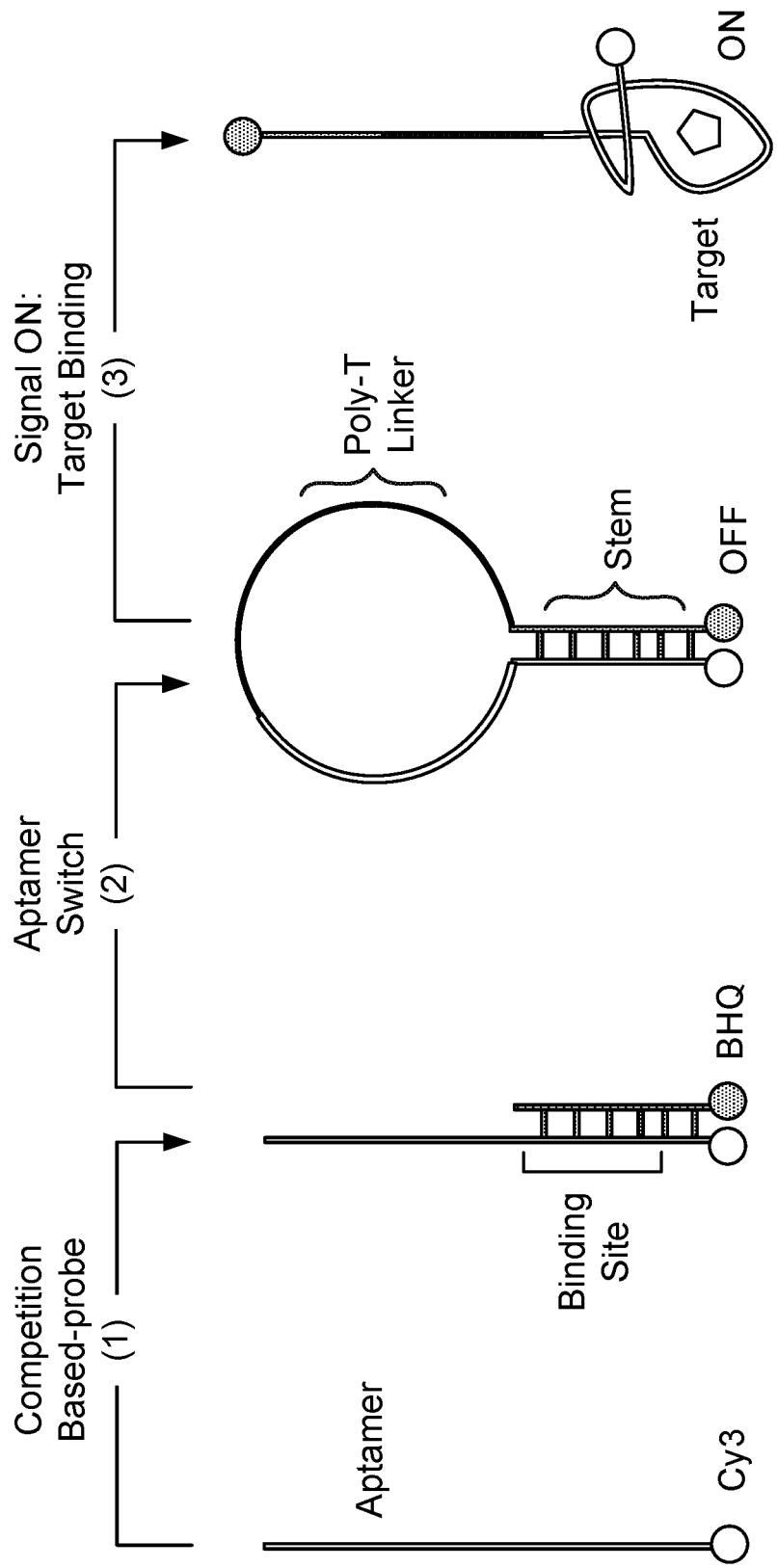
FIG. 19 illustrates an engineering principle of fabricating aptamer switches according to some embodiments.

To demonstrate the feasibility of the strategy, two published aptamers (ATP and Thrombin) are successfully converted into aptamer-switches. (See, e.g., Tang et al., Aptamer Switch Probe Based on Intramolecular Displacement, *J. Am. Chem. Soc.* 130: 11268-11269 (2008).) As illustrated in FIG. 19, a stem-loop structure is formed with a fluorophore (Cy3) and a quencher (BHQ 1) attached at the two termini of the aptamer strand, utilizing DNA (polyT) as a linker. In this construct, a short DNA competitor hybridizes with a partial section of the aptamer sequence, keeping the fluorophore and quencher in close proximity (signal-off) but allows dehybridization when aptamer binds to the target molecule, and moving the quencher away from the fluorophore (signal-on). By optimizing both the length of the stem and linker strands, it may be possible to tune the responsiveness/characteristics of the aptamer-switch. Once the aptamer-switch is created, the fluorophore-quencher can be readily substituted with a FRET pair for ratiometric fluorescence signal detection.

Figure 20A:
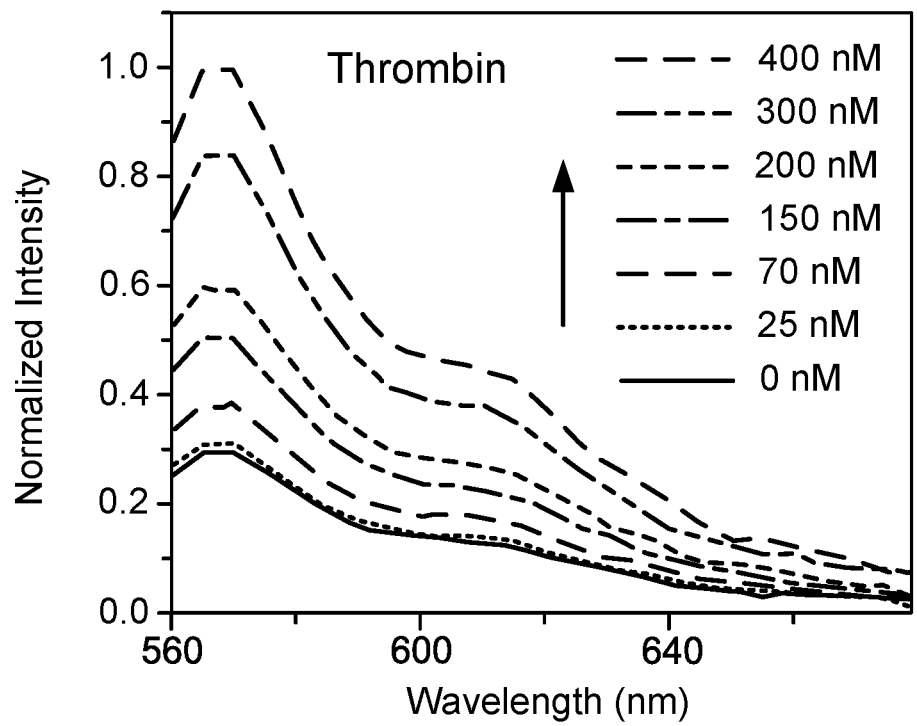
FIGS. 20A and 20B show exemplary plots of the fluorescence intensity spectra of a Thrombin aptamer switch (20A) and ATP aptamer switch (20B) for different target concentrations according to some embodiments.
Figure 20B:
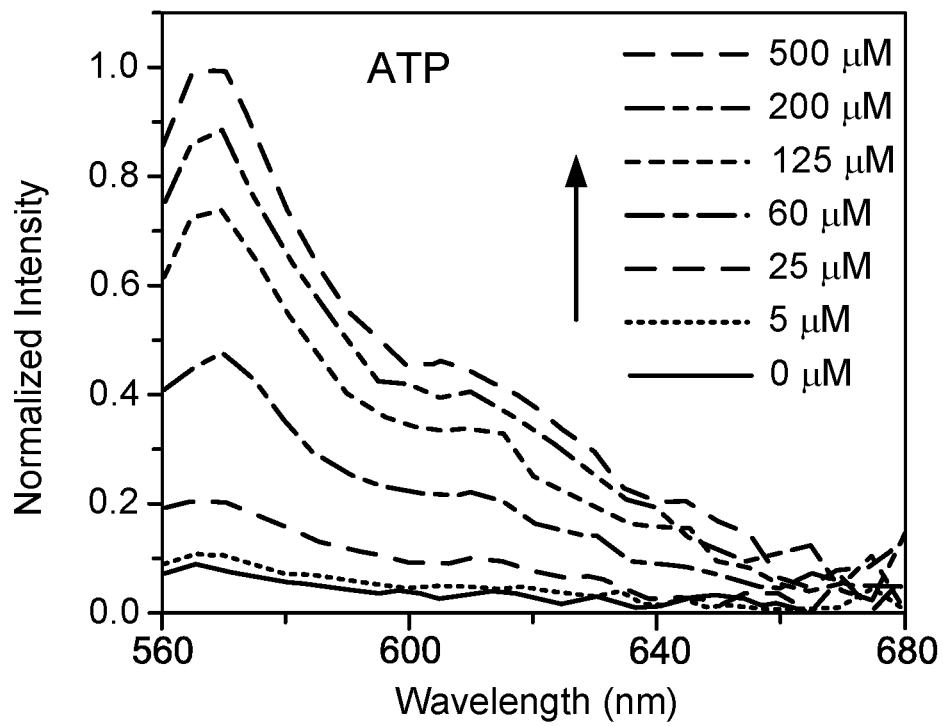

FIGS. 20A-20B show exemplary plots of the fluorescence intensity spectra of the Thrombin/ATP aptamer switch for different target concentrations.

Figure 21:
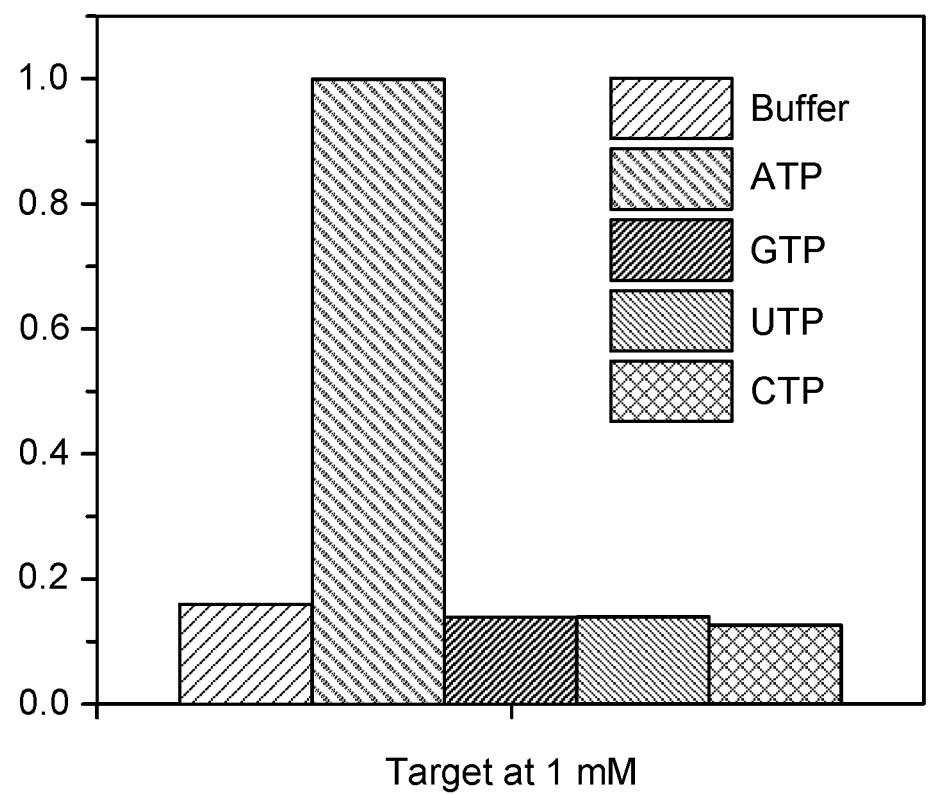
FIG. 21 illustrates selectivity of the ATP aptamer switch according to some embodiments.

FIG. 21 illustrates selectivity for ATP.

C. In Vitro Real Time Measurement

In vitro measurements of ATP and Thrombin are performed using the optical biosensor system with the aptamer switches to test for sensitivity of the system. The optical fiber is placed in a microfluidic chamber (50 uL volume). Target molecules are flowed into the microfluidic chamber at different concentrations using a syringe-pump system.

Figure 22A:
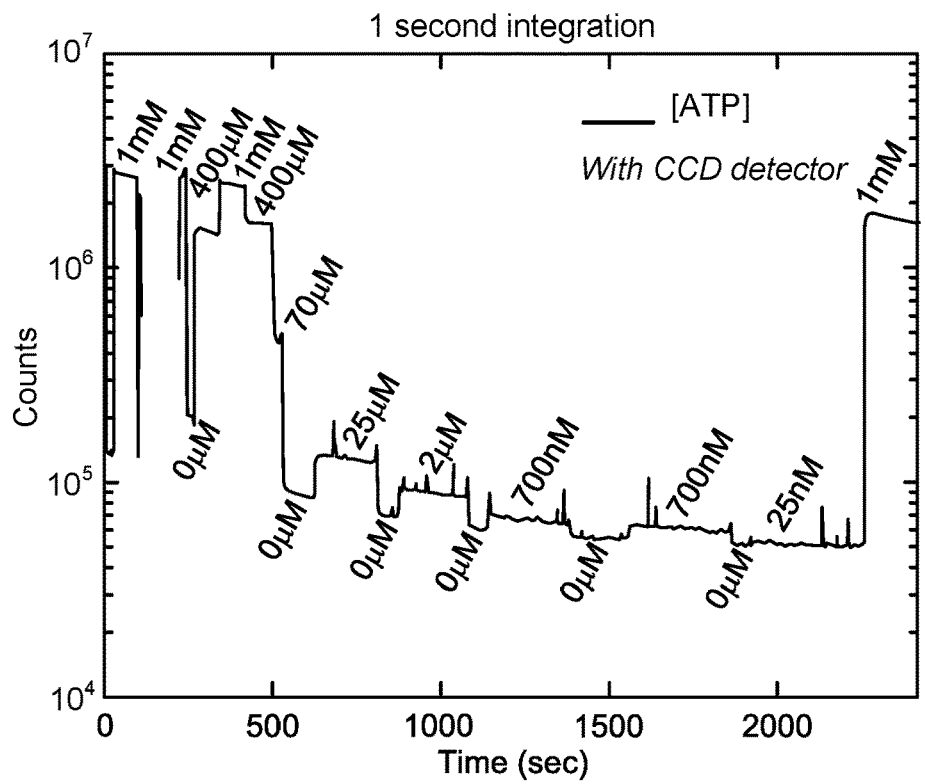
FIG. 22A shows fluorescence intensities measured in real-time monitoring of ATP at different concentrations (e.g., from nM to mM) using an aptamer-based optical probe according to some embodiments.
Figure 22B:
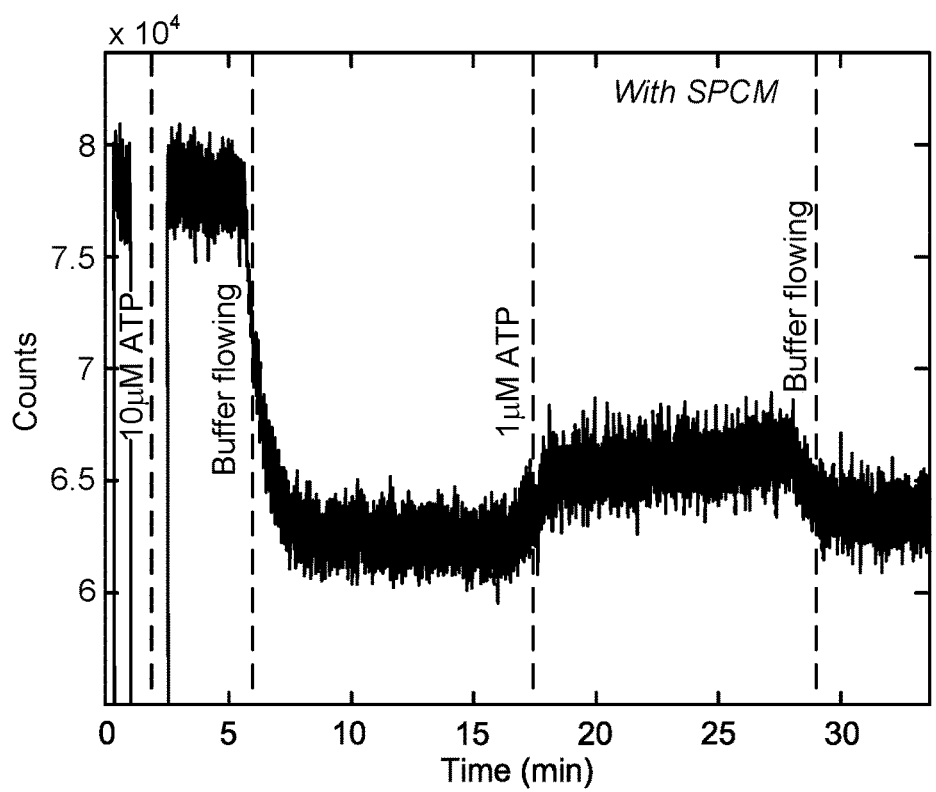
FIG. 22B shows fluorescence intensities measured in real-time monitoring of ATP using an aptamer-based optical probe at different concentrations (e.g., from nM to mM) according to some embodiments.

FIG. 22A shows the fluorescence intensities measured in real-time monitoring of small molecule ATP using an aptamer-based optical probe at different concentrations (e.g., from nM to mM). As illustrated, the optical probe can have high sensitivity down to concentrations in the order of nM.

Figure 23A:
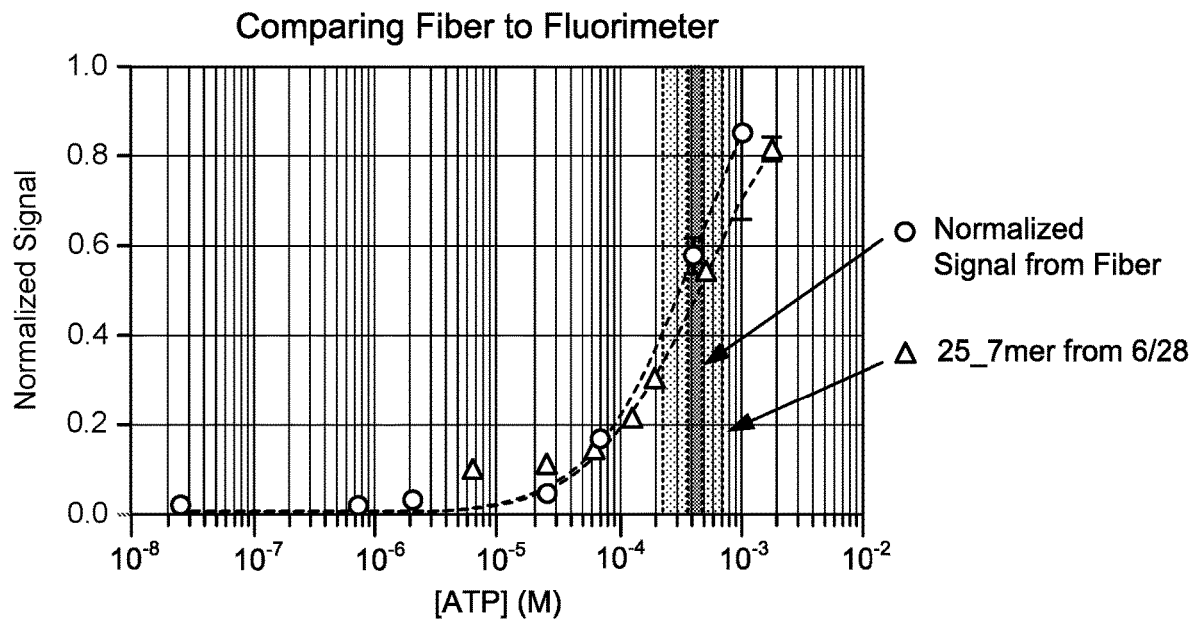
FIGS. 23A and 23B show comparison of signal levels from an optical probe using an optical fiber (circles) and from a fluorimeter (triangles) according to some embodiments. The vertical axis in FIG. 23A is linear, whereas the vertical axis in FIG. 23B is logarithmic.
Figure 23B:
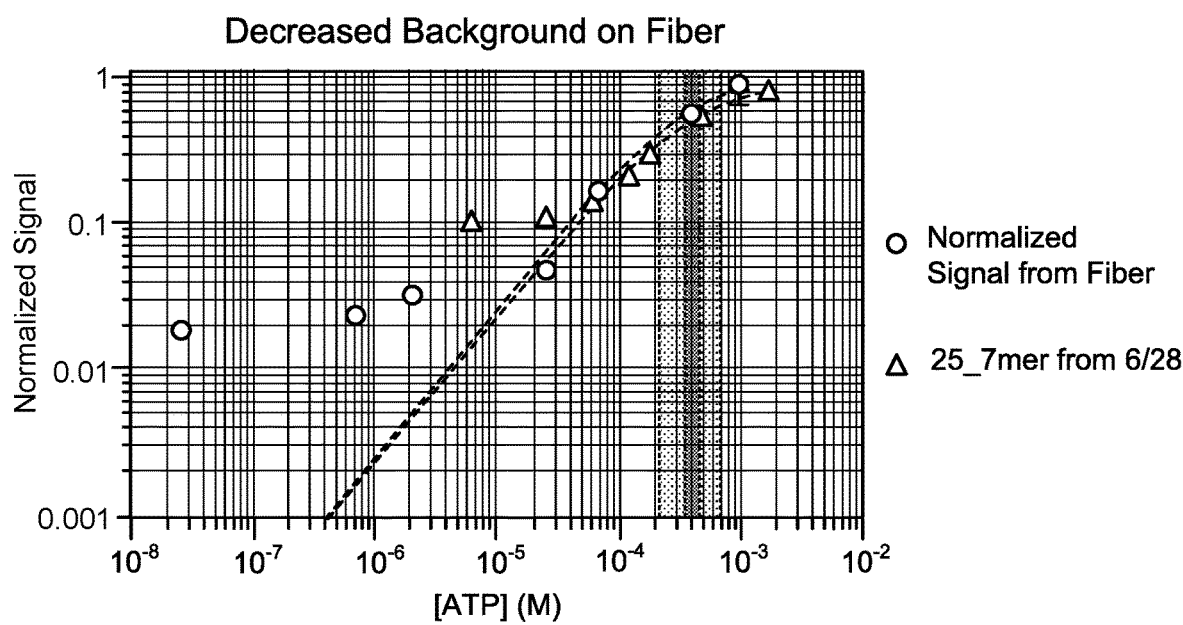

FIGS. 23A and 23B show comparison of signal levels from an optical probe using an optical fiber (circles) and from a fluorimeter (triangles) (the vertical axis in FIG. 23A is linear, whereas the vertical axis in FIG. 23B is logarithmic). As illustrated, the optical probe using an optical fiber has lower background as compared to the fluorimeter.

D. Measurement of Dopamine and Serotonin with Improved Sensitivity and Photostability In some embodiments, the optical biosensor system was used to measure other molecules, such as dopamine (DA) and serotonin (5-hydroxytryptamine receptors or 5-HT receptors). The aptamers for DA and 5-TH are converted into aptamer-switches. (See, e.g., Nakatsuka et al., Aptamer-field-effect Transistors Overcome Debye Length Limitations for Small-molecule Sensing, *Science* 362: 319-324 (2018).) Higher sensitivity and better photostability were achieved through improvements in detector alignment.

To evaluate the performance of the optical biosensor system in a biological matrix, spiked concentration of 5-HT and DA in an artificial cerebrospinal fluid (aCSF) or a cerebrospinal fluid (CSF), and in brain slices mediums were measured using a one-color optical biosensor system.

Figure 24:
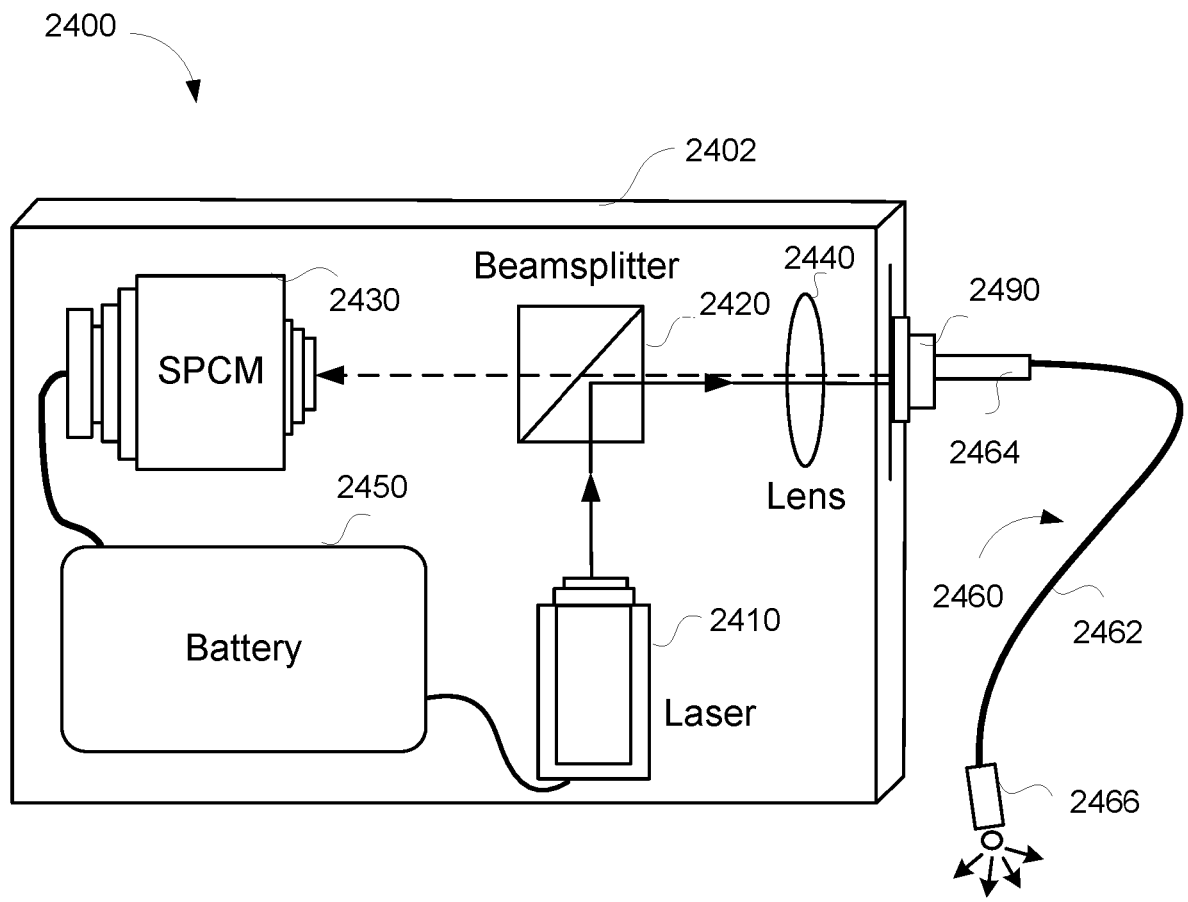
FIG. 24 shows a schematic diagram of the one-color optical biosensor system according to some embodiments.

FIG. 24 shows a schematic diagram of the one-color optical biosensor system 2400 according to some embodiments. The optical biosensor system 2400 includes a laser source 2410, an optical beam splitter 2420, and a detector 2430. The optical biosensor system 2400 may include an optional battery for providing power to the laser source 2410 and the detector 2430. The laser source 2410 is configured to emit a light beam in a first wavelength (e.g., corresponding to green light). The light beam is incident on the optical beam splitter 2420. The optical beam splitter 2420 is configured to reflect the light beam at the first wavelength. The optical biosensor system 2400 may also include a lens 2440 to focus the light beam. The laser source 2410, the optical beam splitter 2420, the detector 2430, and the lens 2440 may be housed within an enclosure 2402.

The optical biosensor system 2400 also includes an optical probe 2460. The optical probe 2460 includes an optical waveguide 2462 such as an optical fiber. The optical waveguide 2462 has a first end 2464 and a second end 2466 opposite to the first end 2464. The first end 2464 of the optical waveguide 2462 may be attached to the enclosure 2402 via a waveguide connector 2490. The light beam focused by the lens 2440 may be coupled into the first end 2464 of the optical waveguide 2462, and be subsequently propagated through the optical waveguide 2462 and be emitted from the second end 2466.

Molecular switches (not shown) are attached to the second end 2466 of the optical waveguide 2462. The send end 2466 of the optical waveguide 2462 may be inserted into an aCSF, CSF, or brain slices. When target molecules, such as dopamine or serotonin, bind to the molecular switches, the molecular switches may emit fluorescence light. The fluorescence light may have a second wavelength that is longer than the first wavelength of the excitation light. The emitted fluorescence light may be coupled back into the optical waveguide 2462 through the second end 2466 and be propagated through the optical waveguide 2462 to be emitted from the first end 2464.

The fluorescence light emitted from the second end 2464 of the optical waveguide 2462 may be collimated by the lens 2440 and incident on the optical beam splitter 2420. The optical beam splitter 2420 is configured to transmit the fluorescence light. In some embodiments, the optical beam splitter 2420 may be a dichroic beam splitter configured to have a high reflectance value for the first wavelength of the excitation light, and a high transmittance value for the second wavelength of the fluorescence light. The fluorescence light transmitted through the optical beam splitter 2420 may be detected by the detector 2430. In some embodiments, the detector 2430 may include a single photon counting module (SPCM).

Figure 25A:
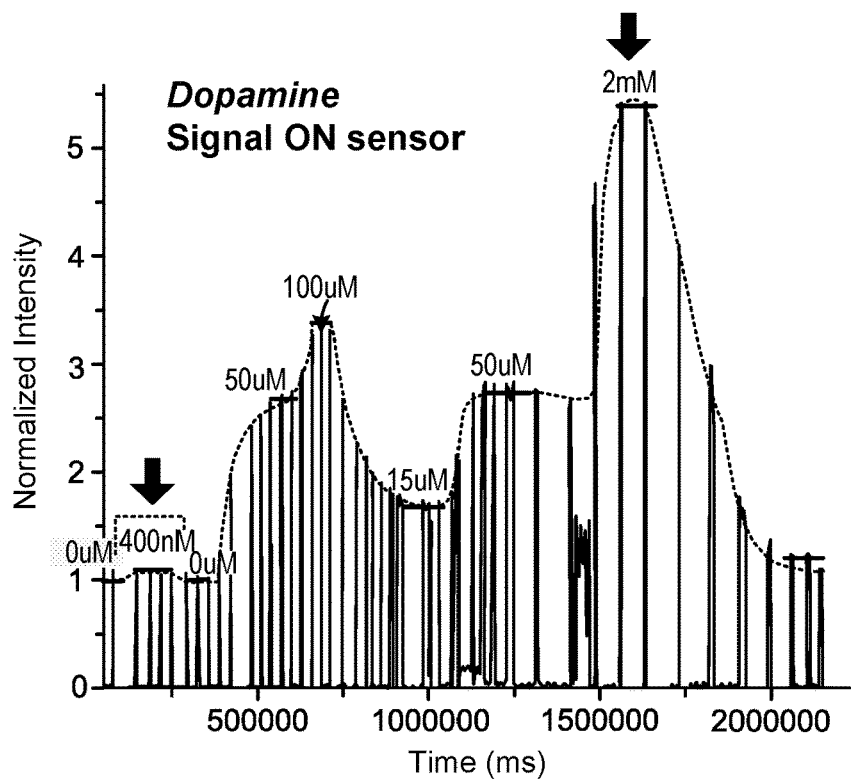
FIG. 25A shows a real-time measurement of optical signal intensity as a function of time upon dopamine binding according to some embodiments.

FIG. 25A shows a real-time measurement of optical signal intensity as a function of time upon dopamine binding. The molecular switches used in the optical probe include signal-on aptamers. Upon binding to dopamine, the fluorescence signal emitted by the fluorophores increases.

Figure 25B:
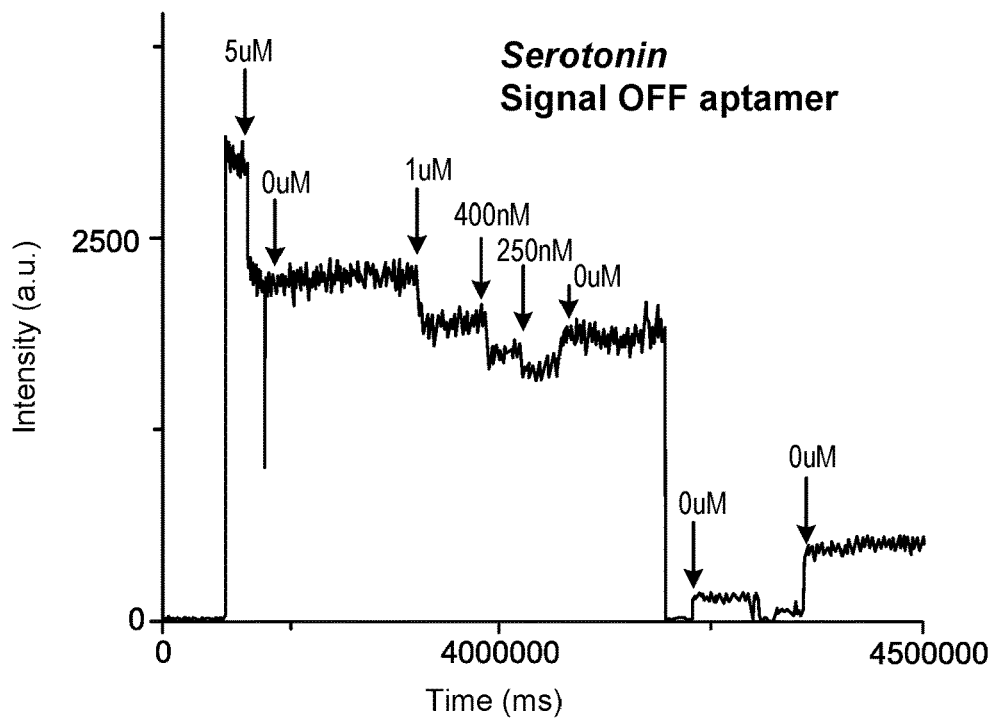
FIG. 25B shows a real-time measurement of optical signal intensity as a function of time upon serotonin (5-HT) binding according to some embodiments.

FIG. 25B shows a real-time measurement of optical signal intensity as a function of time upon serotonin (5-HT) binding. The molecular switches used in the optical probe include signal-off aptamers. Upon binding to 5-HT, the fluorescence signal emitted by the acceptor fluorophores decreases. As illustrated, optical responses differentiated nM-μM concentrations of 5-HT with a good signal-to-noise-ratio (SNR), minimal photobleaching, and high specificity. Sensor responses to dopamine, epinephrine, and the serotonin metabolite 5-hydroxyindoleacetic acid were negligible.

In order to maximize the signal from the fiber tip only, improvements to the alignment and the gain of the detector (SPCM) was made. Such improvements enhanced significantly the collection efficiency and sensitivity. It was demonstrated that the number of counts collected at only 80 nW laser power was very close to the number of counts obtained at 8 μW laser power. The optimized set up enabled the measurement of a descent signal from the very end of the fiber.

Figure 26:
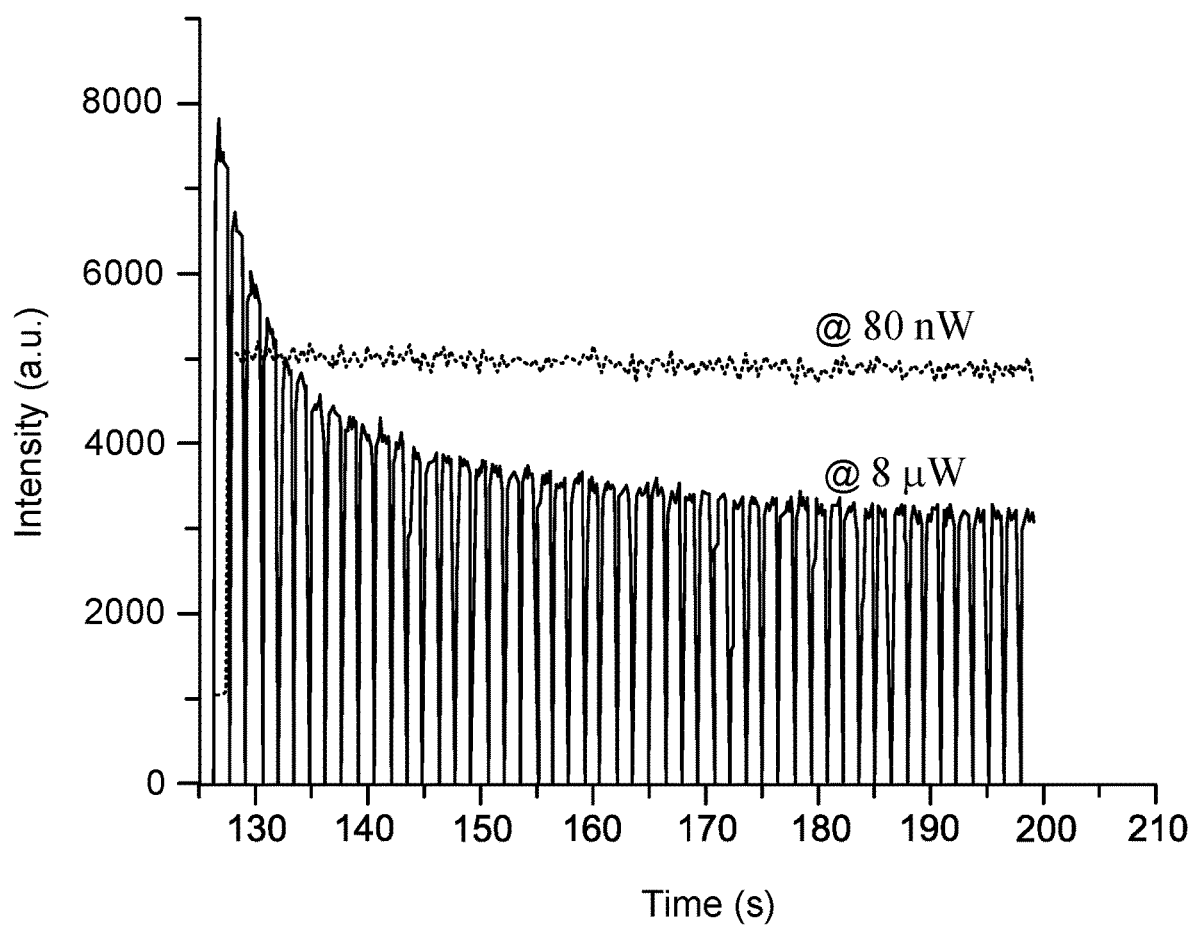
FIG. 26 shows signal intensity as a function of time at a laser power of 8 µW, and signal intensity as a function of time at a laser power of 80 nW, according to some embodiments.

The optimized set up also prevented photobleaching problems, as only the minimal nW power is required. FIG. 26 shows signal intensity as a function of time at a laser power of 8 μW, and signal intensity as a function of time at a laser power of 80 nW. As illustrated, at the laser of power of 8 μW, the signal intensity decreases as time lapses due to photobleaching. In contrast, at the laser power of 80 nW, upon continuous excitation of the fiber-tethered aptamer, a stable fluorescent response was observed over minutes, indicating the stability of the optical biosensor with minimal photobleaching.

Figure 27A:
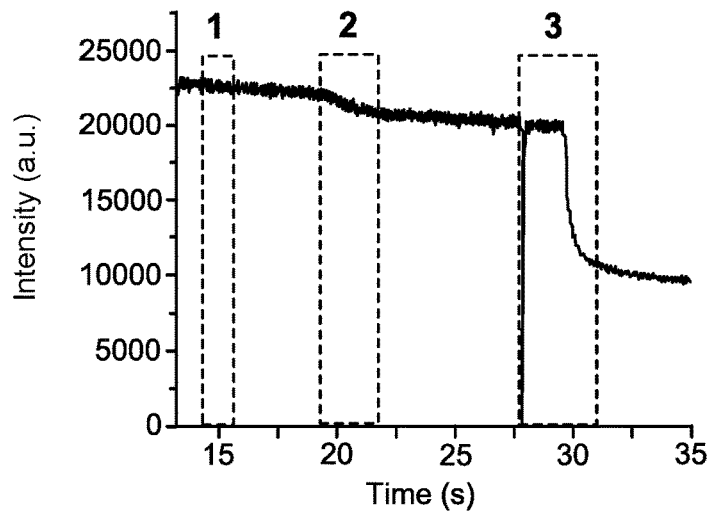
FIG. 27A shows a real-time measurement of optical signal intensity as a function of time upon serotonin binding according to some embodiments.
Figure 27B:
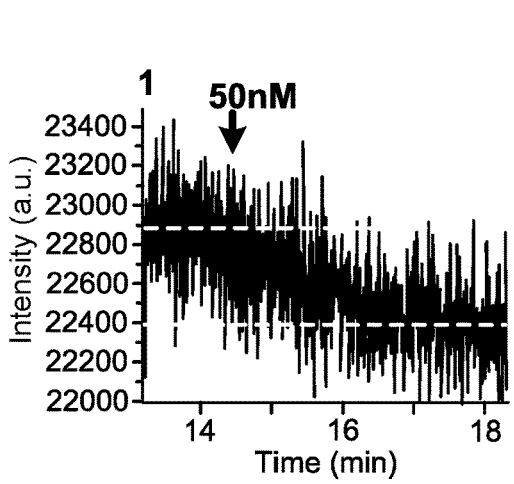
FIGS. 27B, 27C, and 27D show enlarged plots for time regions 1, 2, and 3 shown in FIG. 27A, respectively.
Figure 27C:
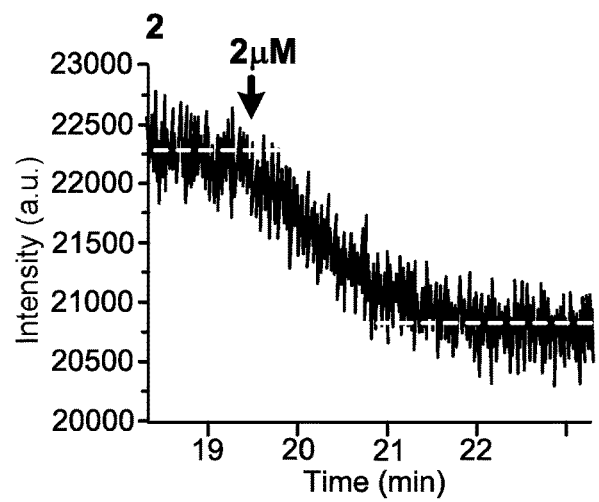
Figure 27D:
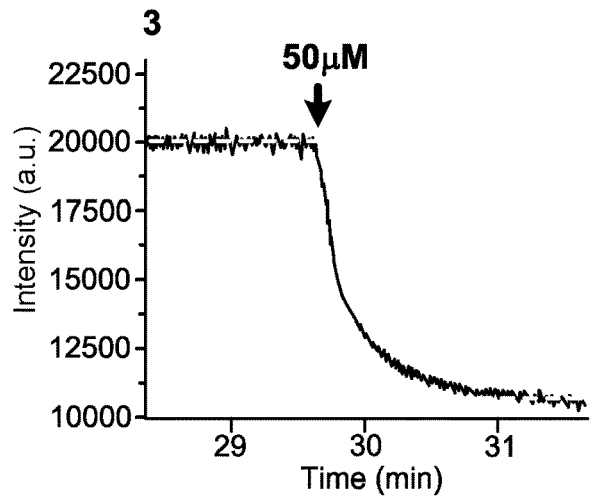

FIG. 27A shows a real-time measurement of optical signal intensity as a function of time upon serotonin binding. FIGS. 27B, 27C, and 27D show enlarged plots for time regions 1, 2, and 3 shown in FIG. 27A, respectively. The optical signal intensity changes as the concentration of 5-HT spiked into the brain slices increases or decreases. As illustrated, a detection limit in the mid-nM range was achieved.

E. Two-Color Optical Biosensor System

In some embodiments, a two-color optical biosensor system is used to monitor both donor fluorescence intensity and acceptor fluorescence intensity as a function of time. The two-color optical biosensor system may minimize false-positive artifacts (e.g., a signal drop) that can be caused by photobleaching, quenching of fluorescence through electron transfer, laser fluctuation, detachment of probes from the surface, and the like. In a two-color optical biosensor system, the donor fluorophore can emit a first optical signal at the emission wavelength of the donor fluorophore and the acceptor fluorophore can emit a second optical signal at the emission wavelength of the acceptor fluorophore. The first optical signal and the second optical signal are at different levels when the molecular switch is not bound to the target molecule compared to when the molecular switch is bound to the target molecule. In certain embodiments, the first optical signal is higher than the second optical signal. In other embodiments, the first optical signal is lower than the second optical signal.

Depending on the set up of the a two-color optical biosensor system, in some embodiments, when the molecular switch is bound to the target molecule, the donor fluorophore and the acceptor are in proximity of each other to produce a FRET signal. In other embodiments, when the molecular switch is not bound to the target molecule, the donor fluorophore and the acceptor are in proximity of each other to produce a FRET signal. This method is sometimes referred to herein as "ratiometric" because it can involve taking the ratio of two colors from the donor fluorophore and the acceptor fluorophore, allowing for more precise measurement of target molecule concentration.

Figure 28:
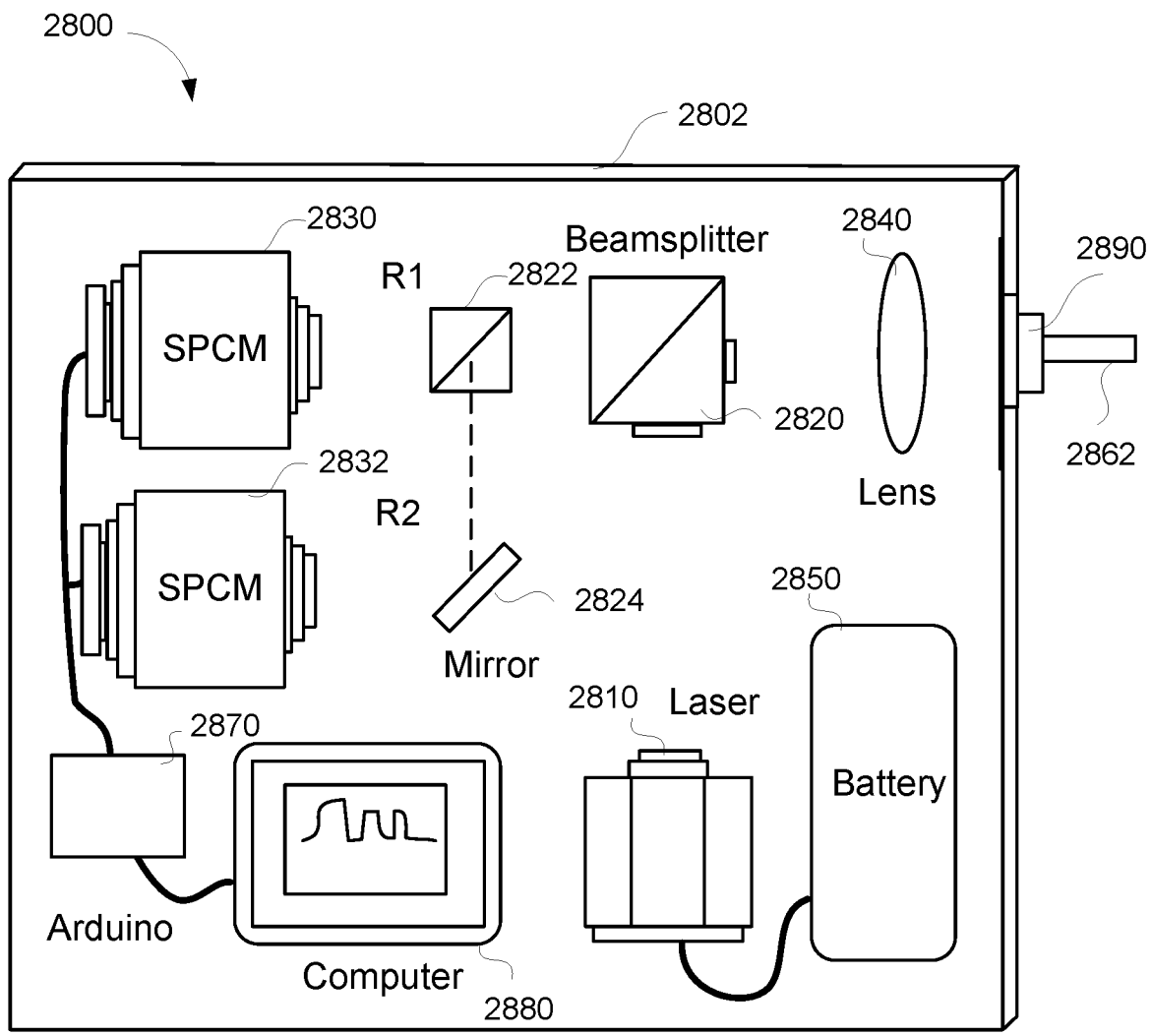
FIG. 28 shows a schematic diagram of a two-color optical biosensor system according to some embodiments.

FIG. 28 shows a schematic diagram of a two-color optical biosensor system 2800 according to some embodiments. The optical biosensor system 2800 includes a laser source 2810, a first optical beam splitter 2820, a second optical beam splitter 2822, a mirror 2824, a first detector 2830, and a second detector 2832. The optical biosensor system 2800 may also include a lens 2840, and an optional battery 2850 for providing power to the laser source 2810. The optical biosensor system 2800 may also include a microcontroller 2870 (e.g., an Arduino single-board microcontroller) and a computer 2880. The various components may be housed within an enclosure 2802.

The laser source 2810 is configured to emit a light beam at a first wavelength. The light beam is incident on the first optical beam splitter 2820. The first optical beam splitter 2820 is configured to reflect the light beam at the first wavelength toward the lens 2840. The lens 2840 focuses the light beam and couples the light beam into an optical waveguide 2862 attached to the enclosure 2802 via a waveguide connector 2890. The optical waveguide 2862 is part of an optical probe, similar to the optical probe 2460 in the optical biosensor system 2400 discussed above. Upon binding to target molecules, the donor and acceptor fluorophores attached to the molecular switches of the optical probe may emit fluorescence light in a second wavelength and a third wavelength, respectively. The fluorescence light emitted by the donor and acceptor fluorophores may be coupled back into the optical waveguide 2862 and be emitted from the first end of the optical waveguide 2862 toward the lens 2840.

The lens 2840 may collimate and project the fluorescence light toward the first optical beam splitter 2820. The first optical beam splitter 2820 may be configured to transmit the fluorescence light at both the second wavelength and the third wavelength. The transmitted fluorescence light is incident on the second optical beam splitter 2822, which is configured to transmit the fluorescence light at the second wavelength, and reflect the fluorescence light at the third wavelength. In some embodiments, the second optical beam splitter 2822 may be a dichroic beam splitter. The fluorescence light transmitted by the second optical beam splitter is detected by the first detector 2830. The fluorescence light reflected by the second optical beam splitter is subsequently reflected by the mirror 2824 toward the second detector 2832 and is detected by the second detector 2832. The first detector 2830 and the second detector 2832 may be SPCMs for sensitive detection. The computer 2880 may be coupled to the first detector 2830 and the second detector 2832 via the microcontroller 2870 for processing the fluorescence signals measured by the first detector 2830 and the second detector 2832.

Figure 29:
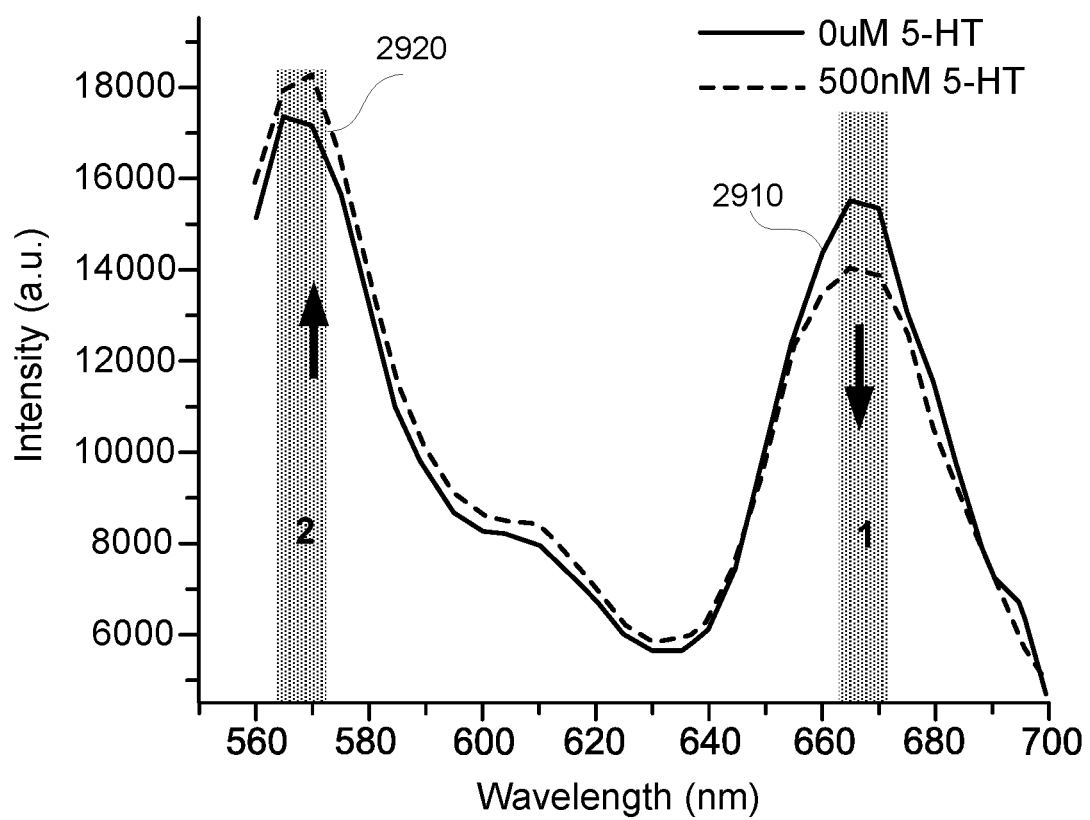
FIG. 29 shows optical signal intensity spectra at two different 5-HT concentrations according to some embodiments.

FIG. 29 shows optical signal intensity spectra 2910 and 2920 at two different 5-HT concentrations (e.g., at 0 μM and 500 nM). As illustrated, both spectra 2910 and 2920 exhibit a first spectral peak at about 570 nm wavelength (corresponding to green light), and a second spectral peak at about 667 nm wavelength (corresponding to red light). The first spectral peak is due to fluorescence light emitted by the donor fluorophores (Cy3); and the second spectral peak is due to fluorescence light emitted by the acceptor fluorophores (Cy5). As the 5-HT concentration is increased from 0 µM to 500 nM, the intensity of the first peak increases, while the intensity of the second peak decreases. In some embodiments, the first detector 2830 may detect fluorescence signals at the 570 nm wavelength (referred herein as the "green channel), and the second detector 2832 may detect fluorescence signals at the 667 nm wavelength (referred herein as the "red channel").

Figure 30A:
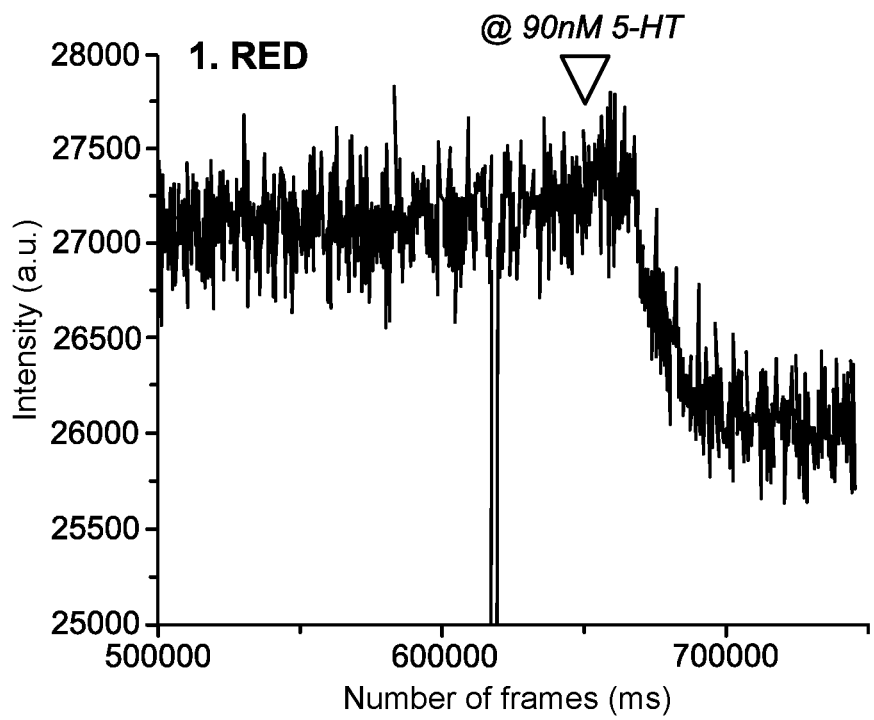
FIG. 30A shows the fluorescence intensity as a function of time measured by the red channel according to some embodiments
Figure 30B:
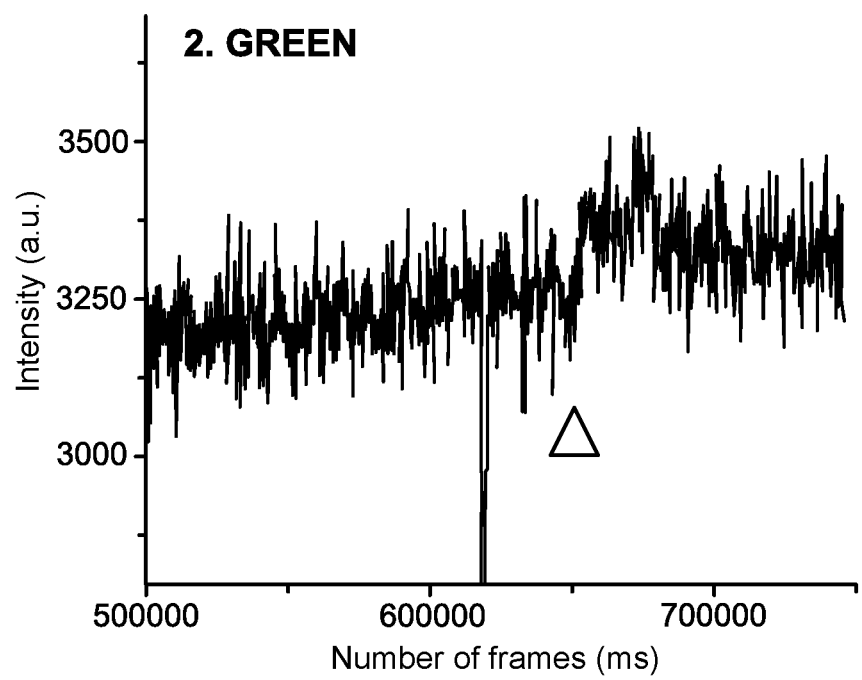
FIG. 30B shows the fluorescence intensity as a function of time measured by the green channel according to some embodiments.

FIG. 30A shows the fluorescence intensity as a function of time measured by the red channel. FIG. 30B shows the fluorescence intensity as a function of time measured by the green channel. As illustrated, upon the addition of 90 nM 5-HT, the acceptor signal (Cy5, red channel) decreases correlated with an increase in the donor signal (Cy3, green channel). Thus, using the two-color optical biosensor system 2800, a sensitivity in the mid-nM level is achieved.

F. In Vivo Detection of Serotonin in Live Brain Slices

According to some embodiments, to measure endogenous release of DA and 5-HT upon drug (MDMA) stimulation with the optical biosensor in live brain slices, a rig system and a brain slice recording chamber are installed in a lab with all the necessary components, including: a gravity-perfusion system alimented by peristatic pump, temperature controller, oxygen lines, microscope, camera and microstage. It was noted that black curtains covering the entire rig system were necessary to minimize the background and fluctuations from room-light.

Initially, the optical fiber was successfully inserted in a brain slice without compromising or breaking the microsize tip of the optical fiber. However, due to mechanical contact, the fluorescence signal was mostly lost during the insertion process. Subsequently, the fiber was protected by a capillary tube from mechanical breakage during the transfer processes onto the rig holder and bath. The protection provided by the capillary helped minimize signal loss due to tip breakage through the transfer process.

Figure 31A:
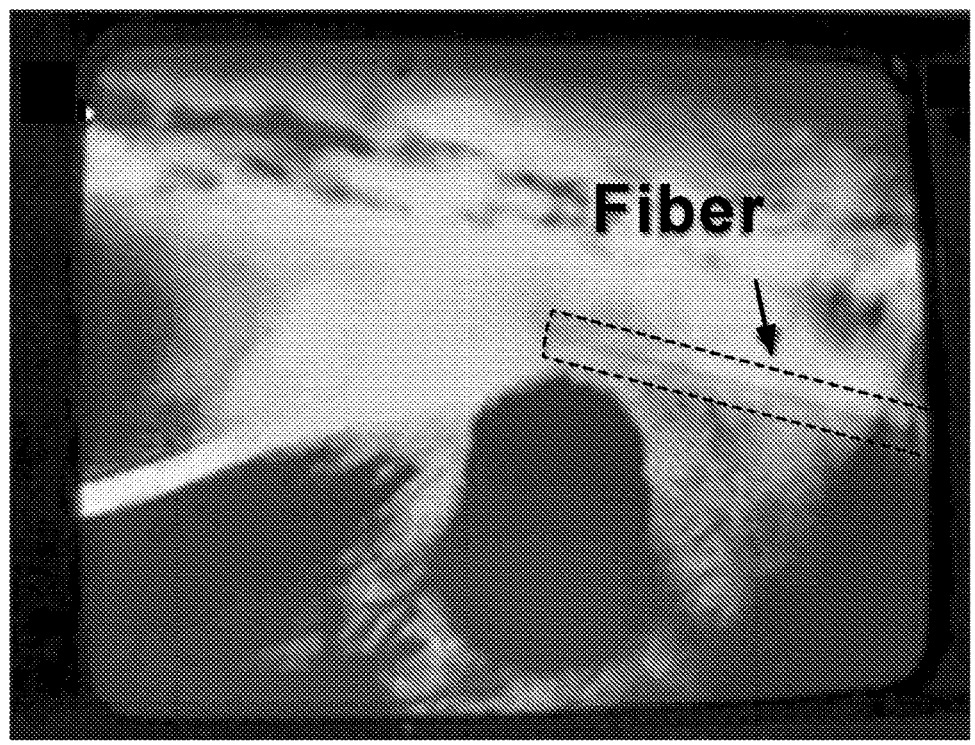
FIG. 31A shows an image of an optical fiber sensor inserted in the nucleus accumbens (NAc) brain region of a mouse according to some embodiments.
Figure 31B:
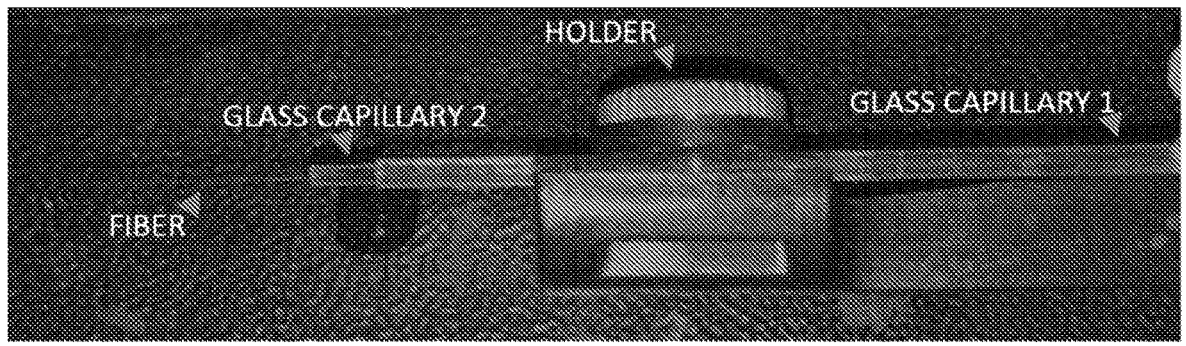
FIG. 31B shows an enlarged image of the optical fiber protected by a capillary according to some embodiments.
Figure 31C:
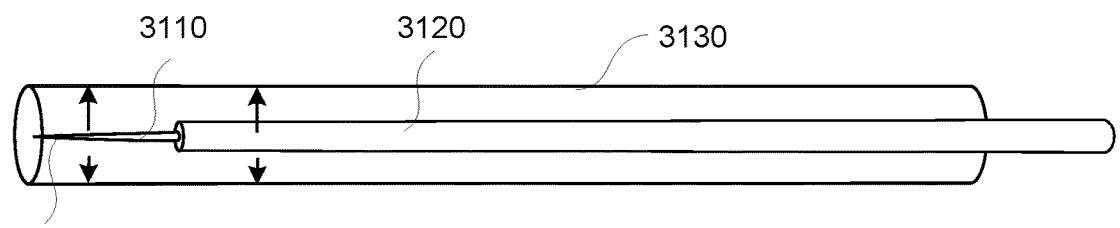
FIG. 31C shows a schematic illustration of the optical fiber sensor configuration according to some embodiments.

FIG. 31A shows an image of an optical fiber sensor inserted in the nucleus accumbens (NAc) brain region of a mouse. FIG. 31B shows an enlarged image of the optical fiber protected by a capillary. FIG. 31C shows a schematic illustration of the optical fiber sensor configuration. The end 3110 of an optical fiber 3120 is stripped off of the protective sleeve and is tapered at the tip 3112. The end 3110 of the optical fiber 3120 is protected by a capillary 3130. The tip 3112 of the optical fiber 3120 is tethered with serotonin aptamers.

The stability of the fluorescence signal over time is characterized in a bath system (rig) under the appropriate conditions favorable for live brain slice measurements. This includes keeping the temperature of the bath at 37° C., with oxygenated artificial CSF (aCSF) flown in the chamber at a rate of 3 ml/min. A stable fluorescence signal (counts) was observed over tens of minutes under continuous laser excitation, which confirmed the robustness of the aptamers, fluorophores and the surface under such conditions. To test the specificity of the aptamers, an excess of MDMA (30 µM) was spiked in a control sample in the absence of brain slice. Minimal change was observed in the fluorescence signal after spiking the excess of MDMA, which confirmed the specificity of the aptamers against the drug used.

After confirming the sensitivity, robustness, and specificity of the aptamer sensor in the rig system, test measurements were performed with live brain slices. After brain removal, blocked hemispheres were mounted and 250 µm thick slices were cut on a vibratome (Leica, VT1200S) in ice-cold sucrose solution. The brain slices were immediately transferred to a bath containing artificial cerebrospinal fluid (aCSF) and warmed to 35° C. The bath also contained the following chemicals (in mM): 124 NaCl, 2.5 KCl, 10 glucose, 26 $NaHCO_3$, 1 $NaH_2PO_4$, 2.5 $CaCl_2$) and 1.3 $MgSO_4$. After 30 minutes, the brain slices were maintained at room temperature for at least one hour prior to being transferred to the recording chamber. The cutting and recording solutions were saturated with 95% 02 and 5% $CO_2$, pH 7.4. Upon transferring to the recording chamber, the brain slices were completely submerged and continuously superfused at a flow rate of 3 mL per minute with aCSF. After mounting the optical fiber sensor onto a holder, the optical fiber sensor was advanced and inserted into the brain slices, placed approximately 300 µm within the tissue. After approximately 10 minutes of baseline measurements (aCSF) to determine the stability of the fluorescence signal in the brain environment over time and estimate the photobleaching rate, drug infusion at 5 µM MDMA was started for 10 minutes.

Figure 32A:
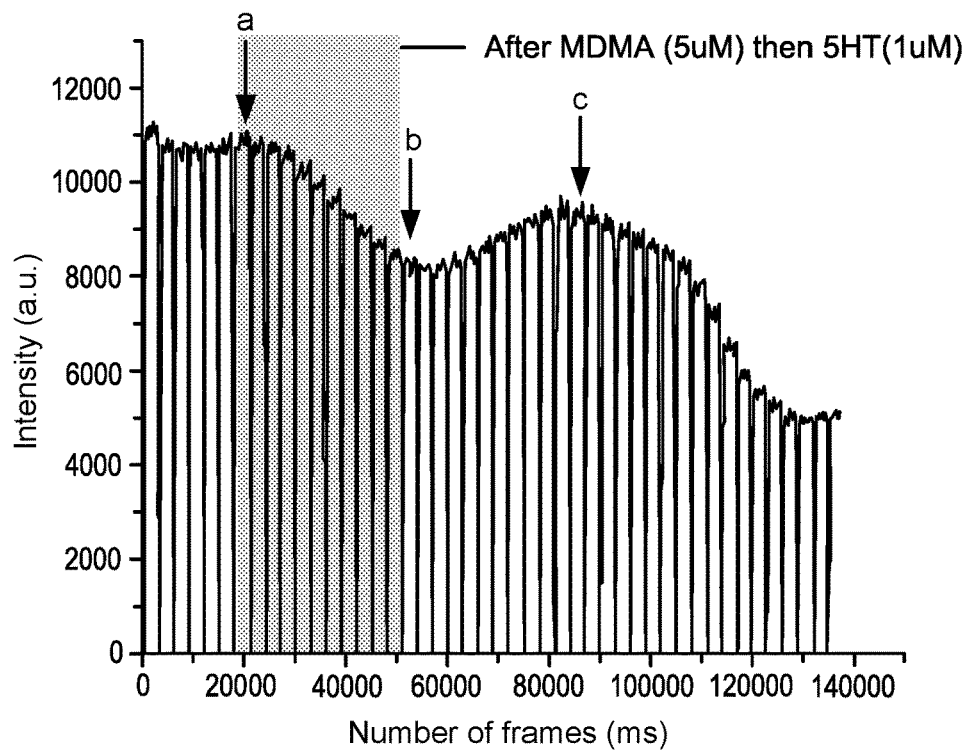
FIGS. 32A and 32B show real-time measurements of fluorescence intensities as a function of time detected by the red channel (Cy5 acceptor signal) and by the green channel (Cy3 donor signal), respectively, of the optical fiber sensor inserted in live brain slices according to some embodiments.
Figure 32B:
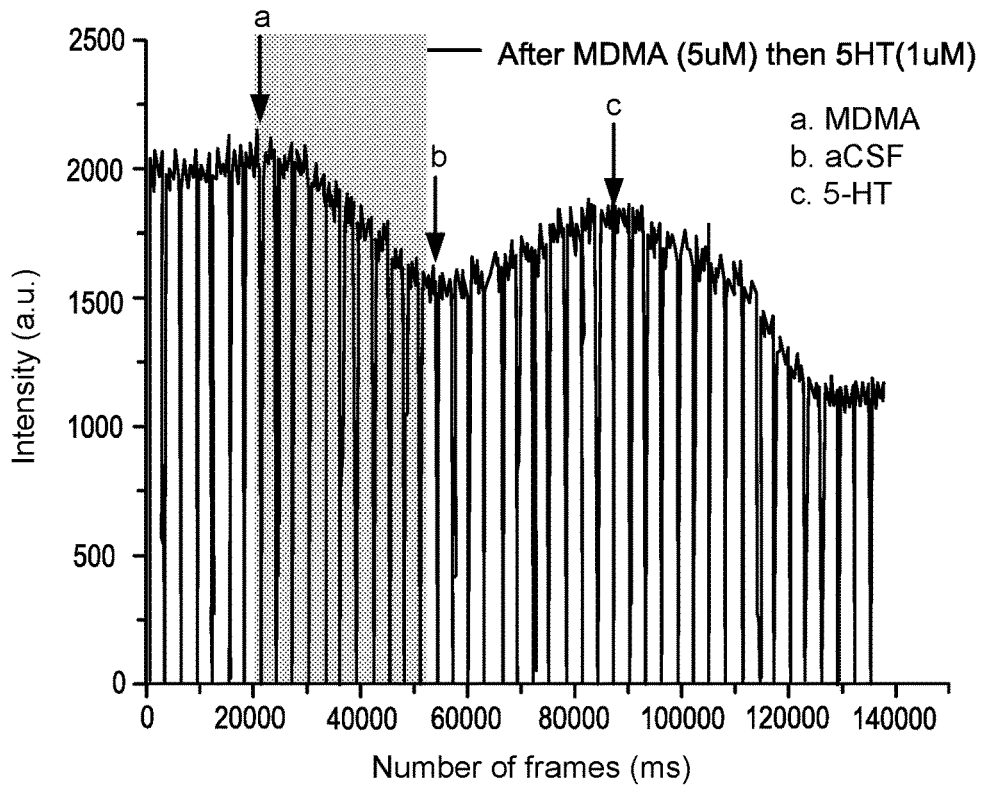

FIGS. 32A and 32B show real-time measurements of fluorescence intensities as a function of time detected by the red channel (Cy5 acceptor signal) and by the green channel (Cy3 donor signal), respectively, of the optical fiber sensor inserted in live brain slices under laser excitation of 532 nm wavelength. As illustrated, a clear drop in the fluorescence intensity was observed in both the red channel and the green channel following the infusion of 5 µM MDMA (at the time instant "a" in FIGS. 32A and 32B). A partial recovery of the fluorescence signal was detected after washing off the MDMA solution with aCSF (at the time instant "b" in FIGS. 32A and 32B). To determine whether the observed drop of the fluorescence signal was caused primarily by serotonin release in the NAc following the infusion of MDMA, a solution of 5-HT (500 nM) was spiked onto the same brain slice (at the time instant "c" in FIGS. 32A and 32B). A similar drop of the fluorescence signal was observed in both the red channel and the green channel. This could be the first instance of detection of endogenous release of serotonin in live brain slices in real-time.

Note that there is leakage from the red channel into the green channel, due to the shoulder of fluorescence spectrum of the red dye that contributes to the green channel signal, and the red channel signal being much higher than the green channel signal. Therefore, a large drop in the red channel signal may induce a drop in the green channel signal.

Despite the recent advances in the field of biosensing achieved through electrochemical methods, these platforms still suffer from many limitations. Among the common disadvantages of electrochemical sensors: (1) limited sensitivity; (2) the sensor drift—sensitive to fluctuating pressure/temperature and must be recalibrated if the environment changes; (3) the sensor lacks long-term stability (electrode degradation); and (4) electrical interference from samples.

In contrast, the optical probes as described herein offer numerous advantages over previous electrochemical approaches. For example, the following advantages may be achieved: (1) very high sensitivity from the optical detectors, (2) near-field effect virtually eliminates background signal, (3) minimal drift through ratio-metric detection (e.g. FRET), (4) highly stable and insensitive to the environment, (5) small size of fibers offers high spatial resolution and ease of multiplexing through fiber bundles, and (6) the ability for continuous monitoring of samples without addition of additional reagents aside from the probe itself.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES

[1] Ho, H. P., et al. "Real-time optical biosensor based on differential phase measurement of surface plasmon resonance." *Biosensors and Bioelectronics*, vol. 20, 28 Oct. 2004, pp. 2177-2180., doi: 10.1016/j.bios.2004.09.011.
[2] Tierney, Sven, et al. "Determination of Glucose Levels Using a Functionalized Hydrogel-Optical Fiber Biosensor: Toward Continuous Monitoring of Blood Glucose in Vivo." *Analytical Chemistry*, vol. 81, 1 May 2009, pp. 3630-3636., doi:10.1021/ac900019k.
[3] Yetisen, Ali K., et al. "Glucose-Sensitive Hydrogel Optical Fibers Functionalized with Phenylboronic Acid." *Advanced Materials*, vol. 29, 2017, pp. 1606380., doi: 10.1002/adma.201606380.
[4] Tian, Ye, et al. "Tapered Optical Fiber Sensor for Label-Free Detection of Biomolecules." *Sensors*, vol. 11, 28 Mar. 2011, pp. 3780-3790., doi:10.3390/s110403780.
[5] Biran, Israel, et al. "Optical imaging fiber-based live bacterial cell array biosensor." *Analytical Biochemistry*, vol. 315, 2003, pp. 106-113., doi:10.1016/S0003-2697 (02)00700-5.
[6] Jia, Kun, et al. "A lower limit of detection for atrazine was obtained using bioluminescent reporter bacteria via a lower incubation temperature." *Ecotoxicology and Environmental Safety*, vol. 85, 2 Aug. 2012, pp. 221-226., http://dx.doi.org/10.1016/j.ecoenv.2012.07.009.
[7] Polyak, Boris, et al. "Bioluminescent whole cell optical fiber sensor to genotoxicants: system optimization." *Sensors and Actuators B*, vol. 3536, 2000, pp. 1-9., doi:0925-4005/00/$.
[8] Oroszlan, P., et al. "Fiber-optic Atrazine immunosensor." *Sensors and Actuators B*, vol. 11, 1993, pp. 301-305.
[9] Miyajima, Kumiko, et al. "Fluorescence immunoassay using an optical fiber for determination of *Dermatophagoides farinae* (Der f 1)." *Environmental Monitoring and Assessment*, vol. 182, 2011, pp. 233-241, doi: 10.1007/s10661-011-1872-6.
[10] Wang, Ruoyu, et al. "A reusable aptamer-based evanescent wave all-fiber biosensor for highly sensitive detection of Ochratoxin A." *Biosensors and Bioelectronics*, vol. 66, 5 Nov. 2014, pp. 11-18., http://dx.doi.org/10.1016/j.bios.2014.10.079.
[11] Tang, Yunfei, et al. "Reusable Split-Aptamer-Based Biosensor for Rapid Detection of Cocaine in Serum by Using an All-Fiber Evanescent Wave Optical Biosensing Platform." *Analytica Chimica Acta*, vol. 933, 24 May 2016, pp. 182-188., doi:10.1016/j.aca.2016.05.021.
[12] Lai, Yu-Hung et al. "Fiber taper characterization by optical backscattering reflectometry." *Optics Express*, vol. 25, 18 Sep. 2017, pp. 22312-22327, https://doi.org/10.1364/OE.25.022312.

What is claimed is:

1. A method of detection of a target molecule in a sample using an optical sensor system, the method comprising:
   contacting the one or more molecular switches of an optical probe to the sample;
   emitting the excitation light from the light source; and
   measuring continuously, using the detector, changes of the optical signals, thereby detecting a concentration of the target molecule in the sample;
   wherein the optical probe comprises:
      an optical waveguide having a first end and a second end, the first end configured to receive excitation light to be propagated through the optical waveguide and to be emitted from the second end or a middle region into a surrounding medium;
      one or more molecular switches attached to a facet or a sidewall of the second end or the middle region of the optical waveguide, wherein the molecular switches are configured to change conformation upon binding to a corresponding target molecule; and
      one or more optical reporters, the optical reporters attached to a respective molecular switch and configured, when exposed to the excitation light, to produce an optical signal that changes upon binding of the respective molecular switch to the corresponding target molecule in the surrounding medium, wherein the optical signal is coupled back into the optical waveguide and propagated through the optical waveguide to be emitted from the first end or second end;
   wherein the optical sensor system comprises:
      the optical probe;
      a light source configured to emit the excitation light to be coupled into the optical waveguide of the optical probe;
      a detector configured to (i) receive the optical signals produced by the one or more optical reporters that are transmitted through the optical waveguide, and (ii) detect changes of the optical signals, thereby allowing for detection of a concentration of the corresponding target molecule;
   wherein the sample is an in vivo tissue of a living subject and the method further comprises administering an amount of an agent to the living subject, and adjusting the amount of the agent based on the detected concentration of the target molecule in the sample.

2. The method of claim 1, wherein the adjusting is determined by a feedback control mechanism configured to adjust the amount of the agent based on the detected concentration of the target molecule in the sample as measured by the optical sensor system.

3. The method of claim 1, wherein the optical waveguide comprises an optical fiber.

4. The method of claim 3, wherein the optical fiber comprises one of a single-mode optical fiber, a step-index multimode optical fiber, or a graded-index multimode optical fiber.

5. The method of claim 1, wherein at least a first molecular switch of the one or more molecular switches is attached to the sidewall of the second end of the optical waveguide, and the respective optical reporter attached to the first molecular switch is exposed to an evanescent optical field of the excitation light adjacent the sidewall.

6. The method of claim 1, wherein at least a first molecular switch of the one or more molecular switches is attached to the sidewall of the middle region of the optical waveguide, and the respective optical reporter attached to the first molecular switch is exposed to an evanescent optical field of the excitation light adjacent the sidewall.

7. The method of claim 6, wherein the evanescent optical field extends to a distance less than one micron from the sidewall.

8. The method of claim 1, wherein the one or more optical reporters comprise one or more fluorescent labels.

9. The method of claim 1, wherein each molecular switch comprises a nucleic acid, a protein, a polymer comprising nucleic acids and proteins, or a chemically modified version thereof.

10. The method of claim 1, wherein:
the one or more molecular switches comprise at least a first molecular switch and a second molecular switch, wherein the first molecular switch changes conformation upon binding to a first target molecule, and the second molecular switch changes conformation upon binding to a second target molecule; and
the one or more optical reporters comprise at least a first optical reporter and a second optical reporter, wherein the first optical reporter is attached to the first molecular switch and configured to produce a first optical signal in a first wavelength range upon binding to the first target molecule, and the second optical reporter is attached to the second molecular switch and configured to produce a second optical signal in a second wavelength range different from the first wavelength range upon binding to the second target molecule.

11. The method of claim 1, wherein the excitation light is in a first wavelength range, and the optical signals produced by the one or more optical reporters are in a second wavelength range different from the first wavelength range, and the optical sensor system further comprising an optical filter coupled to the detector and configured to transmit the optical signals in the second wavelength range and block the excitation light in the first wavelength range.

12. The method of claim 1, wherein the excitation light is in a first wavelength range, wherein the optical signals produced by the one or more optical reporters are in a second wavelength range different from the first wavelength range, and the detector comprises an optical spectrometer.

13. The method of claim 1, wherein the optical probe further comprises a tube surrounding the second end of the optical waveguide, the tube being configured to protect the second end of the optical waveguide when inserted into the sample.

14. The method of claim 1, wherein the system comprises at least a first optical probe and a second optical probe, wherein
the first optical probe comprises:
a first optical waveguide having a first end and a second end, the first end configured to receive excitation light to be propagated through the first optical waveguide and to be emitted from the first end or the second end into a surrounding medium;
one or more first molecular switches attached to a facet or a sidewall of the second end or a middle region of the optical waveguide, wherein the first molecular switches are configured to change conformation upon binding to a corresponding first target molecule; and
one or more first optical reporters, the first optical reporters attached to a respective molecular switch and configured, when exposed to the excitation light, to produce a first optical signal change upon binding of the respective molecular switch to the corresponding first target molecule in the surrounding medium, wherein the first optical signal is coupled back into the optical waveguide via the second end and propagated through the optical waveguide to be emitted from the first end or the second end; and the second optical probe comprises:
a second optical waveguide having a first end and a second end, the first end configured to receive excitation light to be propagated through the second optical waveguide and to be emitted from the first end or the second end into a surrounding medium;
one or more second molecular switches attached to a facet or a sidewall of the second end or a middle region of the second optical waveguide, wherein the second molecular switches are configured to change conformation upon binding to a corresponding second target molecule; and
one or more second optical reporters, the second optical reporters attached to a respective molecular switch and configured, when exposed to the excitation light, to produce a second optical signal change upon binding of the respective molecular switch to the corresponding second target molecule in the surrounding medium, wherein the second optical signal is coupled back into the optical waveguide via the second end and propagated through the second optical waveguide to be emitted from the first end or the second end.

15. A method of detection of a target molecule in a sample using an optical sensor system, the method comprising:
contacting the one or more molecular switches of an optical probe to the sample;
emitting the excitation light from the light source; and
measuring, using the detector, changes of the optical signals, thereby detecting a concentration of the target molecule in the sample;
wherein the optical sensor system comprises:
the optical probe;
a light source configured to emit the excitation light to be coupled into the optical waveguide of the optical probe;
a detector configured to (i) receive the optical signals produced by the one or more optical reporters that are transmitted through the optical waveguide, and (ii) detect changes of the optical signals, thereby allowing for detection of a concentration of the corresponding target molecule; and
wherein the optical probe comprises:
an optical waveguide having a first end and a second end, the first end configured to receive excitation light to be propagated through the optical waveguide and to be emitted from the second end or a middle region into a surrounding medium;
one or more molecular switches attached to a facet or a sidewall of the second end or the middle region of the optical waveguide, wherein the molecular switches are configured to change conformation upon binding to a corresponding target molecule; and
one or more optical reporters, the optical reporters attached to a respective molecular switch and configured, when exposed to the excitation light, to produce an optical signal that changes upon binding of the respective molecular switch to the corresponding target molecule in the surrounding medium, wherein the optical signal is coupled back into the optical waveguide and propagated through the optical waveguide to be emitted from the first end or second end;
wherein the optical reporters comprise a donor fluorophore and an acceptor fluorophore,
wherein the measuring comprises measuring a first optical signal at the emission wavelength of the donor fluorophore and a second optical signal at the emission wavelength of the acceptor fluorophore, and wherein the first optical signal and the second optical signal are at different levels when the molecular switch is not bound to the target molecule compared to when the molecular switch is bound to the target molecule.

16. The method of claim 15, wherein,
(a) when the molecular switch is bound to the target molecule, the donor fluorophore and the acceptor are in proximity of each other to produce a FRET signal; or
(b) when the molecular switch is not bound to the target molecule, the donor fluorophore and the acceptor are in proximity of each other to produce a FRET signal.

* * * * *